(12) United States Patent
Soh et al.

(10) Patent No.: US 9,200,382 B2
(45) Date of Patent: Dec. 1, 2015

(54) HIGH-STRINGENCY SCREENING OF TARGET-BINDING PARTNERS USING A MICROFLUIDIC DEVICE

(75) Inventors: Hyongsok Soh, Santa Barbara, CA (US); Xinhui Lou, Goleta, CA (US); Eric Lagally, Vancouver (CA)

(73) Assignee: The Regents of the University of California, Oakland, CA (US)

( * ) Notice: Subject to any disclaimer, the term of this patent is extended or adjusted under 35 U.S.C. 154(b) by 1256 days.

(21) Appl. No.: 12/286,965

(22) Filed: Oct. 3, 2008

(65) Prior Publication Data

US 2009/0170718 A1  Jul. 2, 2009

Related U.S. Application Data

(60) Provisional application No. 60/978,081, filed on Oct. 5, 2007.

(51) Int. Cl.
| | |
|---|---|
| *C40B 30/04* | (2006.01) |
| *B01L 3/00* | (2006.01) |
| *C40B 70/00* | (2006.01) |
| *C12N 15/10* | (2006.01) |

(52) U.S. Cl.
CPC ........... *C40B 30/04* (2013.01); *B01L 3/502761* (2013.01); *C12N 15/1013* (2013.01); *C40B 70/00* (2013.01); *B01J 2219/005* (2013.01); *B01J 2219/00563* (2013.01); *B01J 2219/00722* (2013.01); *B01J 2219/00725* (2013.01); *B01J 2219/085* (2013.01); *B01L 2200/0652* (2013.01); *B01L 2400/043* (2013.01); *B01L 2400/0454* (2013.01); *C12N 15/1034* (2013.01)

(58) Field of Classification Search
None
See application file for complete search history.

(56) References Cited

U.S. PATENT DOCUMENTS

| | | | |
|---|---|---|---|
| 5,270,163 A | 12/1993 | Gold et al. | |
| 5,475,096 A | 12/1995 | Gold et al. | |
| 2002/0187501 A1* | 12/2002 | Huang et al. | ....................... 435/6 |
| 2004/0018530 A1 | 1/2004 | Bowser et al. | |
| 2004/0018611 A1* | 1/2004 | Ward et al. | ................. 435/287.2 |
| 2007/0059755 A1 | 3/2007 | Janssen et al. | |
| 2008/0124779 A1 | 5/2008 | Oh et al. | |

OTHER PUBLICATIONS

Berezovski, M. et al., "Nonequilibrium Capillary Electrophoresis of Equilibrium Mixtures: A Universal Tool for Development of Aptamers." *J. Am. Chem. Soc.* vol. 127, pp. 3165-3171 (2005).
Berezovski, M. et al., "Non-SELEX Selection of Aptamers." *J. Am. Chem. Soc.* vol. 128, pp. 1410-1411 (2006).
Bigalke H. et al., "Bacterial Protein Toxins" in *Handbook of Experimental Pharmacology* pp. 406-407 (2000).

(Continued)

*Primary Examiner* — Tracy Vivlemore
*Assistant Examiner* — Karen S Weiler
(74) *Attorney, Agent, or Firm* — Michael B. Rubin; Bozicevic, Field & Francis LLP

(57) ABSTRACT

The invention provides a method of screening a library of candidate agents by contacting the library with a target in a reaction mixture under a condition of high stringency, wherein the target includes a tag that responds to a controllable force applied to the tag, and passing the members of the library through a microfluidic device in a manner that exposes the library members to the controllable force, thereby displacing members of the library that are bound to the target relative to their unbound counterparts. Kits and systems for use with the methods of the invention are also provided.

22 Claims, 10 Drawing Sheets

(56) References Cited

OTHER PUBLICATIONS

Blank M, et al., "Systematic Evolution of a DNA Aptamer Binding to Rat Brain Tumor Microvessels—Selective Targeting of Endothelial Regulatory Protein Pigpen." *J Biol Chem* vol. 276, pp. 16464-16468 (2001).
Bock et al., *Nature*, vol. 355, pp. 564-566 (1992).
Bowser, M. T., "SELEX: Just Another Separation?" *Analyst.* vol. 130 pp. 128-130 (2005).
Bruno JG & Kiel JL, "Use of Magnetic Beads in Selection and Detection of Biotoxin Aptamers by Electrochemiluminescence and Enzymatic Methods." *Biotechniques* vol. 32, pp. 178-180 (2002).
Ciesiolka, J. et al., "Selection of an RNA Domain That Binds Zn2+." *RNA* vol. 1, No. 5, pp. 538-550 (1995).
Cox, J. C. & Ellington, A. D. "Automated Selection of Anti-Protein Aptamers." *Bioorganic & Medicinal Chemistry* vol. 9, No. 10, pp. 2525-2531 (2001).
Cox, J. C. et al., "Automated Selection of Aptamers against Protein Targets Translated in Vitro: From Gene to Aptamer." *Nucleic Acids Research* vol. 30 No. 20, pp. 108 (2002).
Cox, J. C. et al., "Automated RNA selection." *Biotechnology Progress* vol. 14, No. 6, pp. 845-850 (1998).
Daniels, D. A et al., "A Tenascin-C Aptamer Identified by Tumor Cell SELEX: Systematic Evolution of Ligands by Exponential Enrichment." *Proceedings of the National Academy of Sciences of the United States of America* vol. 100, pp. 15416-15421 (2003).
Drabovich, A. et al., "Selection of Smart Aptamers by Equilibrium Capillary Electrophoresis of Equilibrium Mixtures (ECEEM)." *J. Am. Chem. Soc.* 2005, 127, 11224-11225.
Ellington et al., "In Vitro Selection of RNA Molecules that Bind Specific Ligands." *Nature* vol. 346, pp. 818-822 (1990).
Giakoumaki, E. et al., "Combination of Amplification and Post-Amplification Strategies to Improve Optical DNA Sensing." *Biosensors & Bioelectronics* vol. 19, pp. 337-344 (2003).
Golden, M. C., "Diagnostic Potential of PhotoSELEX-Evolved ssDNA Aptamers." *J. Biotechnol.* vol. 81, pp. 167-178 (2000).
Gopinath S.C.B., "Methods Developed for SELEX." *Anal Bioanal. Chem.* vol. 387, No. 1, pp. 171-182 (2007).
Gopinath, S. C. B. et al., "An RNA Aptamer that Distinguishes Between Closely Related Human Influenza Viruses and Inhibits Haemagglutinin-Mediated Membrane Fusion." *Journal of General Virology* vol. 87, pp. 479-487 (2006).
Hermanson GT in *Bioconjugate Techniques*, pp. 146-147 (1996).
Hu XY, et al. "Marker-specific sorting of rare cells using dielectrophoresis." *Proc Natl. Acad. Sci. USA* vol. 102, pp. 15757-15761 (2005).
Inglis DW et al., "Continuous Microfluidic Immunomagnetic Cell Separation." *Appl. Phys Lett.* vol. 85, pp. 5093-5095 (2004).
Jenison, R. D. et al., "High-Resolution Molecular Discrimination by RNA." *Science* vol. 263, pp. 1425-1429 (1994).
Jonsson, M. & Lindberg, U., "A Planar Polymer Microfluidic Electrocapture Device for Bead Immobilization" *J. Micromech. Microeng.* vol. 16, pp. 2116-2120 (2006).
Kirby R, et al. "Aptamer-Based Sensor Arrays for the Detection and Quantitation of Proteins." *Anal. Chem.* vol. 76, pp. 4066-4075 (2004).
Kubik, M. F. et al., "High-Affinity RNA Ligands to Human Alpha-Thrombin." *Nucleic Acids Research* vol. 22, pp. 2619-2626 (1994).
Levine HA & Nilsen-Hamilton M, "A Mathematical Analysis of Selex." *J Comput Biol Chem* vol. 31, pp. 11-35 (2007).
Lilliehorn et al.,"Dynamic Arraying of Microbeads for Bioassays in Microfluidic Channels." *Sensors and Actuators B—Chemical*, vol. 106, No. 2, pp. 851-858 (2005).
Mann D et al., "In Vitro Selection of DNA Aptamers Binding Ethanolamine." *Biochem. Biophys. Res Commun.* vol. 338, pp. 1928-1934 (2005).
Mendonsa, S. D. & Bowser, M. T., "In Vitro Selection of High-Affinity DNA Ligands for Human IgE Using Capillary Electrophoresis." *Anal. Chem.* vol. 76, No. 18, pp. 5387-5392 (2004).
Mendonsa, S. D. & Bowser, M. T., "In vitro evolution of functional DNA using capillary electrophoresis." *J. Am. Chem. Soc.* vol. 126, No. 1, pp. 20-21(2004).
Misono, T. S. & Kumar, P. K. R. "Selection of RNA Aptamers against Human Influenza Virus Hemagglutinin Using Surface Plasmon Resonance." *Anal. Biochem.* vol. 342, No. 2, pp. 312-317 (2005).
Morris K et al., "High Affinity Ligands from in Vitro Selection: Complex Targets." *Proc Natl Acad Sci USA* vol. 95, pp. 2902-2907 (1998).
Murphy, M. B. et al., "An Improved Method for the in Vitro Evolution of Aptamers and Applications in Protein Detection and Purification." *Nucleic Acids Research* vol. 31, No. 18, p. 110 (2003).
Nakajima, N. & Ikeda, Y. "Mechanism of Amide Formation by Carbodiimide for Bioconjugation in Aqueous-Media." *Bioconjugate Chemistry* vol. 6, pp. 123-130 (1995).
Nimjee SM et al., "Aptamers: An Emerging Class of Therapeutics." *Annu Rev Med* vol. 56, pp. 555-558 (2005).
Nitsche A, et al., "One-step Selection of Vaccinia Virus-Binding DNA Aptamers by MonoLEX." *BMC Biotech* vol. 7, pp. 1-12 (2007).
Nkodo, A. E. et al., "Diffusion Coefficient of DNA Molecules During Free Solution Electrophoresis." *Electrophoresis* vol. 22, pp. 2424-2432 (2001).
Nutiu, R. & Li, Y. F. "In vitro selection of structure-switching signaling aptamers." *Angewandte Chemie-International* Edition 44, pp. 1061-1065 (2005).
Oh, S. H. et al., "Microfluidic Protein Detection through Genetically Engineered Bacterial Cells." *Journal of Proteome Research* vol. 5, pp. 3433-3437 (2006).
Pan, W. H. et al., "Isolation of Virus-Neutralizing RNAs from a Large Pool of Random Sequences." *Proceedings of the National Academy of Sciences of the United States of America* vol. 92, pp. 11509-11513 (1995).
Ravelet C et al., "Liquid Chromatography, Electrochromatography and Capillary Electrophoresis Applications of DNA and RNA Aptamers." *J Chromatogr A* vol. 1117 pp. 1-10 (2006).
Shamah SM HJ & Cload ST, "Complex Target SELEX." *Acc Chem. Res.* vol. 41, pp. 130-138 (2008).
Shangguan D, et al., "Cell-Specific Aptamer Probes for Membrane Protein Elucidation in Cancer Cells." *J Proteome Res* vol. 7, pp. 2133-2139 (2008).
Shangguan, D. H. et al., "Aptamers Evolved From Cultured Cancer Cells Reveal Molecular Differences of Cancer Cells in Patient Samples." *Clinical Chemistry* vol. 53, pp. 1153-1155 (2007).
Stoltenburg, R. et al. "FluMag-SELEX as an Advantageous Method for DNA Aptamer Selection." *Analytical and Bioanalytical Chemistry* vol. 383, pp. 83-91 (2005).
Tok JB-H & Fischer NO "Single Microbead SELEX for Efficient ssDNA Aptamer Generation against Botulinum Neurotoxin." *Chem. Commun.* vol. 16, pp. 1883-1885 (2008).
Tombelli S MM & Mascini M, "Aptamers-based Assays for Diagnostics, Environmental and Food Analysis." *Biomol Eng* vol. 24, pp. 191-200 (2007).
Tuerk C & Gold L, "Systematic Evolution of Ligands by Exponential Enrichment—RNA Ligands to Bacteriophage-T4 DNA-Polymerase." *Science* vol. 249, pp. 505-510 (1990).
Ulrich H, et al., "DNA and RNA Aptamers: from Tools for Basic Research towards Therapeutic Applications." *Comb. Chem. High Throughput Screen* vol. 9, pp. 619-632 (2006).
Urvil, P. T. et al., "Selection of RNA Aptamers that Bind Specifically to the NS3 Protease of Hepatitis C Virus." *European Journal of Biochemistry* vol. 248, pp. 130-138 (1997).
Wiegand, T. W. et al., "High-affinity Oligonucleotide Ligands to Human IgE Inhibit Binding to Fc Epsilon Receptor I." *J. Immunol.* vol. 157, pp. 221-230 (1996).
Willner I & Zayats M, "Electronic Aptamer-based Sensors." *Angew Chem. Int.* Edition 46, pp. 6408-6418 (2007).
Xiao Y et al., "Label-free Electronic Detection of Thrombin in Blood Serum by Using an Aptamer-based Sensor." *Angew Chem. Int.* Edition 44, pp. 5456-5459 (2006).
Drabovich et al. (2006) "Selection of Smart Aptamers by Methods of Kinetic Capillary Electrophoresis" Anal Chem 78(9):3171-3178.
Gold (2001) "mRNA Display: Diversity Matters during In Vitro Selection" Proc Natl Acad Sci USA 98Z(9):4825-4826.

(56) References Cited

OTHER PUBLICATIONS

Jhaveri & Ellington (2000) "In Vitro Selection of RNA Aptamers to a Protein Target by Filter Immobilization" Curr Protoc Mol Biol, Chapter 24: Unit 24.3.1-24.3.25, Supplement 52.

Mosing et al. (2005) "Capillary Electrophoresis-SELEX Selection of Aptamers with Affinity for HIV-1 Reverse Transcriptase" Anal Chem 77(19):6107-6112.

Vant-Hull et al. (2000) "Theoretical Principles of In Vitro Selection Using Combinatorial Nucleic Acid Libraries" Curr Protoc Nucleic Acid Chem, Chapter 9:Unit 91.1-9.1.16.

Berezovski, et al; "Nonequilibrium Capillary Electrophoresis of Equilibrium Mixtures—A Single Experiment Reveals Equilibrium and Kinetic Parameters of Protein-DNA Interactions"; J. Am. Chem. Soc. 124; (2002); pp. 13674-13675.

Marshal et al; "In Vitro Selection of RNA Aptamers"; Methods in Enzymology, vol. 318; (2000); pp. 193-214.

Vater et al; "Short bioactive Spiegelmers to migraine-associated calcitonin gene-related peptide rapidly identified by a novel approach: Tailored-SELEX"; Nucleic Acids Research, vol. 31, No. 21; (2003); pp. 1-7.

* cited by examiner

HIGH-STRINGENCY SCREENING OF TARGET-BINDING PARTNERS USING A MICROFLUIDIC DEVICE

CROSS REFERENCE TO RELATED APPLICATION

This application claims priority to U.S. Provisional Patent Application No. 60/978,081 filed Oct. 5, 2007, which is incorporated herein by reference in its entirety and for all purposes.

STATEMENT REGARDING FEDERALLY SPONSORED RESEARCH

This invention was made with government support under grant no. W-7405-ENG-48 awarded by the Department of Energy. The government has certain rights in the invention.

BACKGROUND

Many of the underlying challenges in biochemical library screening arise from the law of mass-action and diffusion. For affinity interactions at chemical equilibrium, the starting biochemical library contains more low-affinity binders than high-affinity binders. Thus, without an engineered intervention, low-affinity binders can "out-compete" the high-affinity binders in early rounds of selection. In addition, the matter is often complicated further by the fact that the number of target molecules is usually greater than the number of high affinity binders, making the selection of high-affinity binders even more difficult in the initial rounds of library screening. The process step at which the high-affinity binders are separated from the low-affinity (and non-) binders is called "molecular partitioning". This separation step is important because it directly affects the number of cycles required to screen through a large population of candidate molecules, and it is usually limited by diffusion during the purification step. Moreover, during this process, selective pressures and biases either intentional or unintentional may affect the overall biochemical properties of the evolved population, and quite often result in unsuccessful screens. Thus, in order to accelerate the process of molecular selection, technology platforms capable of addressing the challenges posed by the laws of mass-action and molecular diffusion are of interest.

LITERATURE

Literature of interest includes: Ellington et al., 1990 *Science* 346, 818-822; Tuerk, C. and Gold, L. 1990 *Science* 249:505-510; Bock et al., 1992 *Nature* 355: 564-566; X. Hu et al. 2005 *PNAS* 102(44); Jonsson, M. and Lindberg, U., 2006 *J. Micromech. Microeng.* 16:2116-2120; Berezovski et al., *J. Am. Chem. Soc.* 2005 127:3165-3171; Mendonsa, S. and Bowser, M., 2004 *J. Am. Chem. Soc.* 126:20-21; Mendonsa, S. and Bowser, M., *Anal. Chem.* 2004 76:5387-5392; Lilliehorn et al., 2005 *Sensors and Actuators B* 106:851-858: U.S. Pat. No. 5,475,096; U.S. Pat. No. 5,270,163; U.S. patent application Ser. No. 11/583,989, filed Oct. 18, 2006; U.S. patent application Ser. No. 11/655,055, filed Jan. 17, 2007; and U.S. Application Publication No. 20040018530.

SUMMARY OF THE INVENTION

The invention provides a method of screening a library of candidate agents by contacting the library with a target in a reaction mixture under a condition of high stringency, wherein the target includes a tag that responds to a controllable force applied to the tag, and passing the members of the library through a microfluidic device in a manner that exposes the library members to the controllable force, thereby displacing members of the library that are bound to the target relative to their unbound counterparts. Kits and systems for use with the methods of the invention are also provided.

In one aspect, the disclosure provides for a library screening method comprising contacting a library of candidate agents with a target in a reaction mixture under a condition of high stringency, wherein said target comprises a tag that responds to a controllable force applied to said tag, and passing the members of the library through a microfluidic device in a manner that exposes said members to said controllable force, wherein members of the library that are bound to the target are displaced relative to their unbound counterparts.

In some embodiments, the condition of high stringency includes providing in the reaction mixture a total number of targets that is at least three orders of magnitude less than the total number of library members. In additional embodiments, the condition of high stringency includes a high-stringency salt concentration in the reaction mixture. The condition of high stringency may also include subjecting the reaction mixture to a high-stringency temperature.

In another aspect, the disclosure provides for a library screening method comprising contacting a library of candidate agents with a target in a reaction mixture under a condition of high stringency, wherein said target comprises a tag that responds to a controllable force applied to said tag, and passing the members of the library through a microfluidic device in a manner that exposes said members to said controllable force, wherein members of the library that are bound to the target are displaced relative to their unbound counterparts, and wherein the method further comprises detecting, amplifying, and/or separating the members of the library that are displaced relative to their unbound counterparts.

In additional embodiments, the library screening methods disclosed herein comprise contacting a library of candidate agents with a target in a reaction mixture under a condition of high stringency, wherein said target comprises a tag that responds to a controllable force applied to said tag, and passing the members of the library through a microfluidic device in a manner that exposes said members to said controllable force, wherein members of the library that are bound to the target are displaced relative to their unbound counterparts, and further wherein the tag is a magnetic bead. In certain embodiments, the tag is negatively charged.

In another aspect, the methods disclosed herein comprise contacting a library of candidate agents with a target in a reaction mixture under a condition of high stringency, wherein said target comprises a tag that responds to a controllable force applied to said tag, and passing the members of the library through a microfluidic device in a manner that exposes said members to said controllable force, wherein members of the library that are bound to the target are displaced relative to their unbound counterparts, and further wherein the application of the controllable force provides for a partition efficiency which is greater than $10^6$.

In some embodiments, the methods disclosed herein comprise contacting an aptamer library with a target in a reaction mixture under a condition of high stringency, wherein said target comprises a tag that responds to a controllable force applied to said tag, and passing the members of the library through a microfluidic device in a manner that exposes said members to said controllable force, wherein members of the library that are bound to the target are displaced relative to their unbound counterparts.

In another aspect, the methods disclosed herein comprise contacting a library of candidate agents with a protein target in a reaction mixture under a condition of high stringency, wherein said target comprises a tag that responds to a controllable force applied to said tag, and passing the members of the library through a microfluidic device in a manner that exposes said members to said controllable force, wherein members of the library that are bound to the target are displaced relative to their unbound counterparts.

In another aspect, the methods disclosed herein comprise contacting a library of candidate agents with a target in a reaction mixture under a condition of high stringency, wherein said target comprises a tag that responds to a controllable force applied to said tag, and passing the members of the library through a microfluidic device in a manner that exposes said members to said controllable force, wherein members of the library that are bound to the target are displaced relative to their unbound counterparts, and further wherein said target is provided in said reaction mixture at a sub-nanomolar concentration.

In another aspect, the methods disclosed herein comprise contacting a library of candidate agents with a target in a reaction mixture under a condition of high stringency, wherein said target comprises a tag that responds to a controllable force applied to said tag, and passing the members of the library through a microfluidic device in a manner that exposes said members to said controllable force, wherein members of the library that are bound to the target are displaced relative to their unbound counterparts, and further wherein, after one round, the members of the library that are displaced relative to their unbound counterparts bind the target molecule with dissociation constants ($K_d$) in a nanomolar or sub-nanomolar range.

In another aspect, the methods disclosed herein comprise contacting a library of candidate agents with a target in a reaction mixture under a condition of high stringency, wherein said target comprises a tag that responds to a controllable force applied to said tag, wherein said controllable force is selected from the group consisting of a magnetic field, an electric field, condensed-light electromagnetic radiation, and acoustic radiation, and passing the members of the library through a microfluidic device in a manner that exposes said members to said controllable force, wherein members of the library that are bound to the target are displaced relative to their unbound counterparts.

In another aspect, the methods disclosed herein comprise passing a reaction mixture comprising a candidate agent and a target through a microfluidic device, wherein said target comprises a tag that responds to a controllable force applied to said tag and wherein said passing exposes said tag to said controllable force, and further wherein said target is immobilized by the exposure of said tag to said controllable force; exposing the immobilized target to a condition of high stringency, wherein said condition of high stringency favors formation of specific target-binding partner complexes. In another aspect, the methods further comprise identifying unbound candidate agents as agents of interest. In an additional embodiment, the methods comprise identifying target-bound candidate agents as agents of interest.

BRIEF DESCRIPTION OF THE DRAWINGS

FIG. 3 is a graph showing a calibration curve used to determine the amount of bead-immobilized BoNT/A-rLc.

Figure 1:
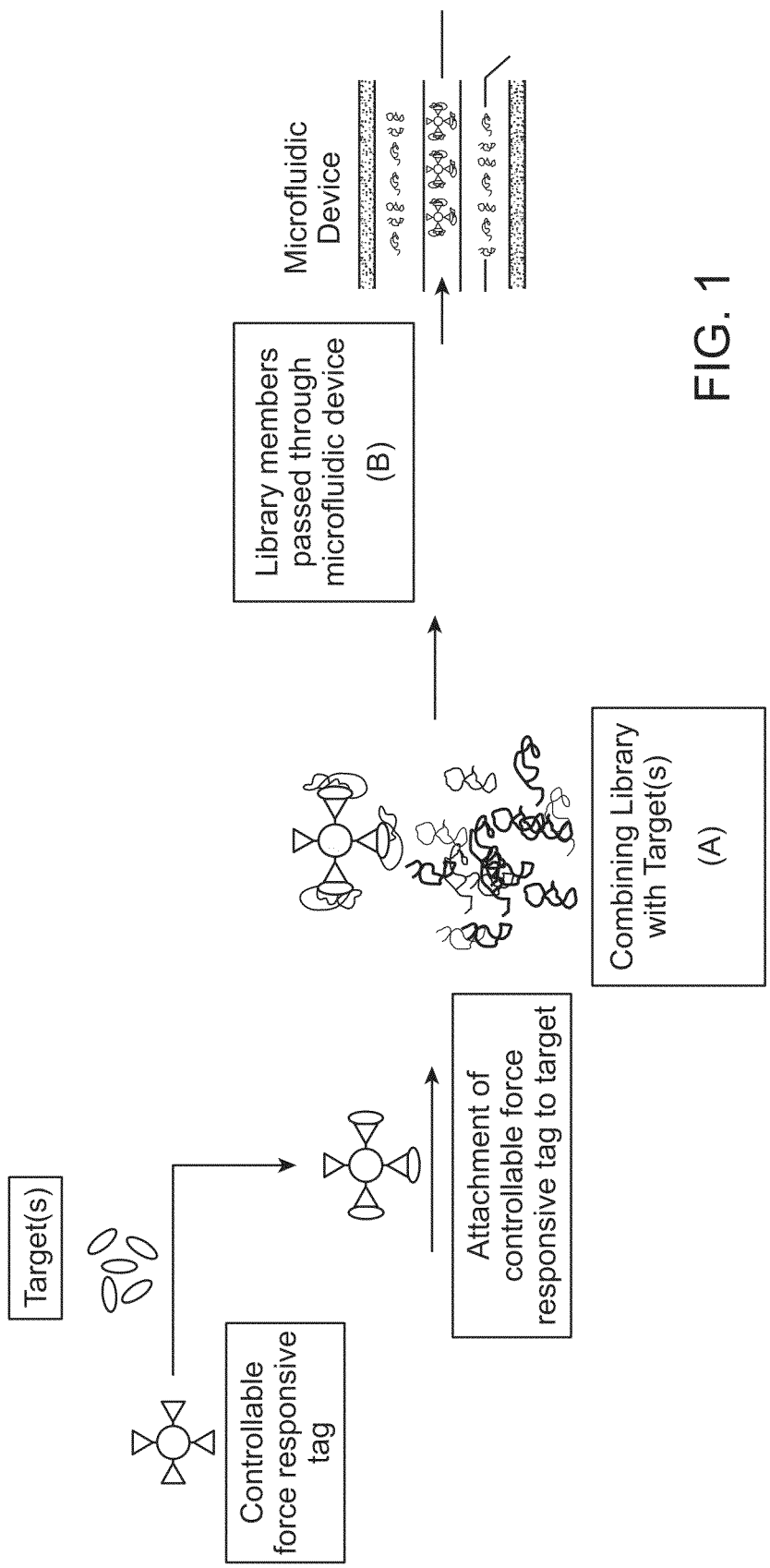
FIG. 1 is a schematic illustrating an exemplary embodiment of the screening methods disclosed herein.

FIG. 4 is a graph showing the activity of bead-bound target via SNAPtide assay.

FIG. 5 is a diagram of an exemplary aptamer library design.

FIG. 6 is a graph showing a real-time PCR calibration curve for partition efficiency measurements.

FIG. 7 is a diagram showing an overview of an aptamer library screen for high-affinity target binders using an exemplary CMACS device.

Figure 8:
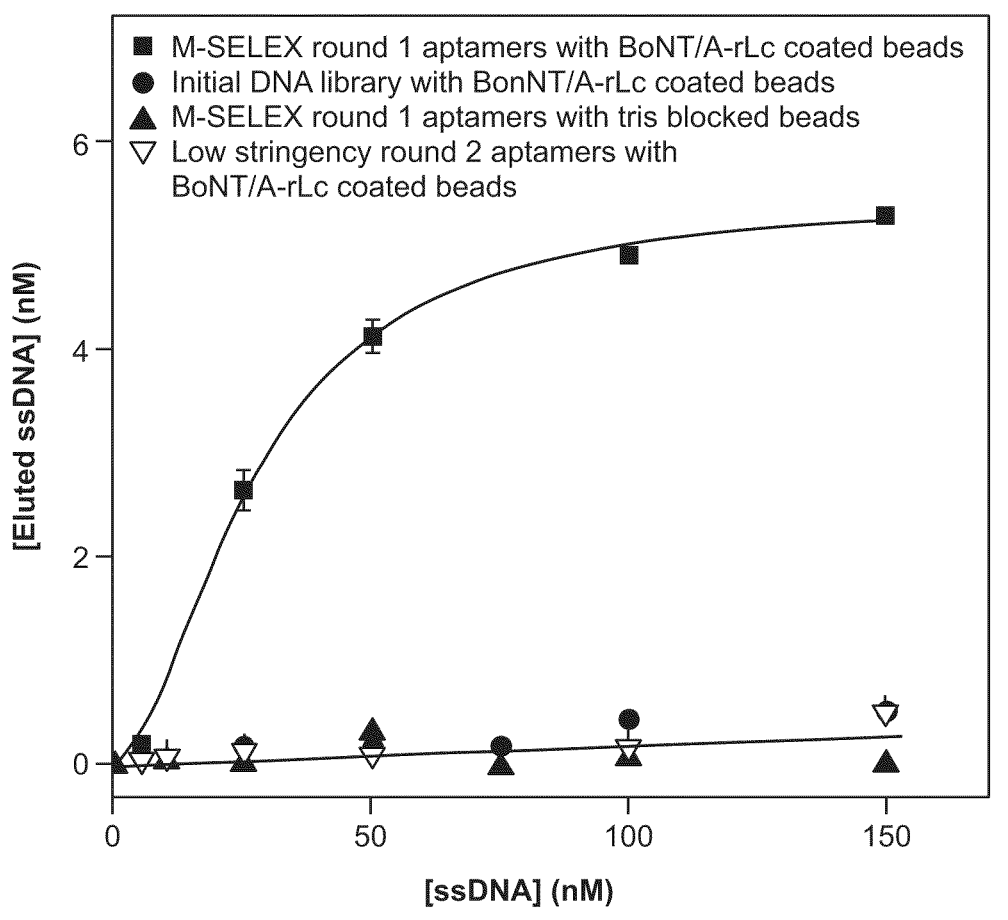

FIG. 8 is a graph showing the determination of the dissociation constant ($K_d$) for a round 1 aptamer library.

FIG. 9 shows an exemplary CMACS device and illustrates the effect of the combination of hydrodynamic ($F_d$) and magnetophoretic forces ($F_m$) imposed on a magnetic bead traveling through an exemplary CMACS device.

FIG. 10 illustrates a method for the fabrication of an exemplary CMACS device.

DEFINITIONS

"Heterologous" in the context of the association between a tag and a target, refers to a target which comprises a tag which is not associated with the target as found in nature or which is not a naturally occurring property of the target.

"Exogenous" in the context of the association between a tag and a target, refers to a target which comprises a tag, wherein the tag is external to the target but positioned with respect to the target such that the application of the controllable force to the tag is effectively applied to the target while maintaining desired activity or other characteristic of the target which is the basis for identification of a candidate binding partner.

"High-affinity" as used herein refers to a $K_d$ value for a binding pair complex, also referred to herein as a candidate target binding agent-target complex or a library member-target complex, of less than or equal to 100 nM and greater than or equal to 10 fM.

"High-avidity" as used herein refers to a $K_d$ value for a binding pair complex, also referred to herein as a candidate target binding agent-target complex or a library member-target complex, of less than or equal to 100 nM and greater than or equal to 10 fM.

One "round" or "cycle" of the screening procedure involves contacting a library of candidate agents with a target in a reaction mixture under a condition of high stringency, wherein said target comprises a tag that responds to a controllable force applied to said tag; and passing the members of the library through a microfluidic device in a manner that exposes said members to said controllable force; wherein members of the library that are bound to the target are displaced relative to their unbound counterparts. The methods disclosed herein may comprise additional rounds or cycles such that the target bound members of the library which are displaced relative to their unbound counterparts are separated from their respective targets and newly contacted with a target according to the first round or cycle of the method. "Separation" in this context can also refer to the amplification of target bound library members, e.g., by the use of a PCR reaction and appropriate primers.

The terms "antibodies" and "immunoglobulin" include antibodies or immunoglobulins of any isotype, fragments of antibodies which retain specific binding to antigen, including, but not limited to, Fab, Fv, scFv, and Fd fragments, chimeric antibodies, humanized antibodies, single-chain antibodies, and fusion proteins comprising an antigen-binding portion of an antibody and a non-antibody protein. The antibodies may be detectably labeled, e.g., with a radioisotope, an enzyme which generates a detectable product, a fluorescent protein, and the like. The antibodies may be further conjugated to other moieties, such as members of specific binding pairs, e.g., biotin (member of biotin-avidin specific binding pair), and the like. The antibodies may also be bound to a solid support, including, but not limited to, polystyrene plates or beads, and the like. Also encompassed by the term are Fab', Fv, F(ab')$_2$, and or other antibody fragments that retain specific binding to antigen, and monoclonal antibodies.

Antibodies may exist in a variety of other forms including, for example, Fv, Fab, and (Fab')$_2$, as well as bi-functional (i.e. bi-specific) hybrid antibodies (e.g., Lanzavecchia et al., *Eur. J. Immunol.* 17, 105 (1987)) and in single chains (e.g., Huston et al., *Proc. Natl. Acad. Sci. U.S.A.*, 85, 5879-5883 (1988) and Bird et al., Science, 242, 423-426 (1988), which are incorporated herein by reference). (See, generally, Hood et al., "*Immunology*.", Benjamin, N.Y., 2nd ed. (1984), and Hunkapiller and Hood, Nature, 323, 15-16 (1986),).

Chimeric antibodies are antibodies whose light and heavy chain genes have been constructed, typically by genetic engineering, from antibody variable and constant region genes belonging to different species. For example, the variable segments of the genes from a rabbit monoclonal antibody may be joined to human constant segments, such as gamma 1 and gamma 3. An example of a therapeutic chimeric antibody is a hybrid protein composed of the variable or antigen-binding domain from a rabbit antibody and the constant or effector domain from a human antibody (e.g., the anti-Tac chimeric antibody made by the cells of A.T.C.C. deposit Accession No. CRL 9688), although other mammalian species may be used.

As used herein, the terms "determining," "measuring," "assessing," and "assaying" are used interchangeably and include both quantitative and qualitative determinations.

The terms "polypeptide" and "protein", used interchangeably herein, refer to a polymeric form of amino acids of any length, which can include coded and non-coded amino acids, chemically or biochemically modified or derivatized amino acids, and polypeptides having modified peptide backbones. The term includes fusion proteins, including, but not limited to, fusion proteins with a heterologous amino acid sequence, fusions with heterologous and native leader sequences, with or without N-terminal methionine residues; immunologically tagged proteins; fusion proteins with detectable fusion partners, e.g., fusion proteins including as a fusion partner a fluorescent protein, β-galactosidase, luciferase, etc.; and the like.

The terms "nucleic acid molecule" and "polynucleotide" are used interchangeably and refer to a polymeric form of nucleotides of any length, either deoxyribonucleotides or ribonucleotides, or analogs thereof. Polynucleotides may have any three-dimensional structure, and may perform any function, known or unknown. Non-limiting examples of polynucleotides include a gene, a gene fragment, exons, introns, messenger RNA (mRNA), transfer RNA, ribosomal RNA, ribozymes, cDNA, recombinant polynucleotides, branched polynucleotides, plasmids, vectors, isolated DNA of any sequence, control regions, isolated RNA of any sequence, nucleic acid probes, and primers. The nucleic acid molecule may be linear or circular.

"Stringency conditions" refers to conditions in a reaction mixture that influence formation of complexes between candidate binding partners.

The term "reaction mixture" as used herein refers to a fluid medium in which a target is contacted with or in contact with a candidate agent(s). This includes, for example, a reaction mixture in which a library of candidate target binding agents is initially contacted with a target and any subsequent wash steps designed to remove non-specific or low-affinity target binding agents. Where desired, the stringency conditions of the reaction mixture can be modified so as to influence the formation of complexes between target and candidate target binding agent(s). Thus, for example, stringency conditions of a reaction mixture during initial contacting of target and a library of candidate binding agents (which may be referred to as "binding conditions") and stringency conditions of a reaction mixture during washing (referred to as "wash conditions", e.g., to disrupt complexes of an undesirably low affinity and/or deplete non-specifically bound candidate agents) may be of the same or different stringencies.

The terms "library member" and "candidate agent" are used interchangeably herein. Where the method involves positive selection for candidate agents that bind to a target, the candidate agents may be referred to as candidate target binding agents.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "and," and "the" include plural referents unless the context clearly dictates otherwise. Thus, for example, reference to "a candidate agent" includes a plurality of such candidate agents and reference to "the candidate agent" includes reference to one or more candidate agents and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

The library screening methods disclosed herein comprise contacting a library of candidate agents with a target in a reaction mixture under a condition of high stringency, wherein said target comprises a tag that responds to a controllable force applied to said tag, and passing the members of the library through a microfluidic device in a manner that exposes said members to said controllable force, wherein members of the library that are bound to the target are displaced relative to their unbound counterparts. The elements of the disclosed methods as well as kits and systems for use with the methods of the invention are discussed in greater detail below.

Targets and Tags

Targets

The methods disclosed herein provide for the high-efficiency screening of libraries comprising candidate agents, e.g., candidate target binding agents. The libraries disclosed herein may be screened against a variety of targets. In general, a suitable target for use in the present methods is any molecule, virus, whole cell, or cellular component, for which a high-affinity binding partner is desired. Many suitable targets are known in the art. Exemplary targets include: peptides, proteins, nucleic acids, viruses, antibodies or fragments thereof (including single chain antibodies, Fabs, and the like), whole cells, cellular components, organic and inorganic small molecules, or combinations thereof.

Protein targets of interest include, for example, cell surface receptors, signal transduction factors, and hormones.

Nucleic acid targets of interest include, for example, DNA and RNA targets, e.g., aptamers.

Cellular targets of interest include, for example, mammalian cells, particularly human cells; stem cells; and bacterial cells.

Antibody targets of interest include antibodies or immunoglobulins of any isotype, fragments of antibodies which retain specific binding to antigen, including, but not limited to, Fab, Fv, scFv, and Fd fragments, chimeric antibodies, humanized antibodies, single-chain antibodies, and fusion proteins comprising an antigen-binding portion of an antibody and a non-antibody protein.

Small molecule targets of interest include both organic and inorganic small molecules.

More than one type of target may be utilized simultaneously in the screening methods disclosed herein. For example, two or more protein targets having different amino acid sequences may be simultaneously screened against a single library, e.g. an aptamer library.

Tags

In the methods disclosed herein, a target with respect to which a corresponding library of candidate agents is to be screened comprises a tag that responds to a controllable force. A tag that responds to a controllable force, also referred to as a "controllable force responsive tag" generally refers to a tag that can be displaced to a second position relative to a first position by the application of the compatible controllable force to the tag. Thus in accordance with the methods disclosed herein, the tag is generally selected so as to be compatible with (i.e., responsive to) the particular controllable force that is to be applied to the target comprising the tag or, stated differently, the controllable force used to displace tagged targets is selected so as to be compatible with the tag. For example, where the controllable force to be applied is a magnetic field, a suitable tag is a magnetic particle or bead.

The tag may be endogenous or intrinsic to a target, e.g., a naturally occurring component of said target which renders the target responsive to a particular controllable force. The tag may also be exogenous (or heterologous) to the target, so that the tag-target combination is not one normally found in nature. Where the tag is either exogenous or heterologous to the target, the tag is positioned with respect to the target such that the application of the controllable force to the tag is effectively applied to the target while maintaining desired activity or other characteristic of the target which is the basis for identification of a candidate binding partner.

The tag may be directly bound to the target or the tag may be indirectly bound to the target via an intermediate, e.g., a linker or a bifunctional reagent. In some cases, the target and the tag may be contacted with a bifunctional reagent having one moiety that binds with a target species and another moiety that binds with the surface of the tag. If the tag particles are coated with streptavidin for example, a suitable bifunctional reagent may be a biotinylated antibody specific for the target in the sample. Exemplary tags include those that are responsive to controllable forces such as magnetic, electric, condensed-light electromagnetic and acoustic forces.

Magnetically-Responsive Tags

An exemplary tag-controllable force combination is the use of a magnetically responsive tag and a magnetic field. In such embodiments, a suitable tag is one that responds to a magnetic field, e.g. a magnetic particle. Magnetic particles which may be utilized in the disclosed methods include, for example, magnetic beads or other small objects made from a magnetic material such as a ferromagnetic material, a paramagnetic material, or a superparamagnetic material. The magnetic particles should be chosen to have a size, mass, and susceptibility that allows them to be easily diverted from the direction of fluid flow when exposed to a magnetic field in a microfluidic device (balancing hydrodynamic and magnetic effects). In certain embodiments, the particles do not retain magnetism when the field is removed. In one embodiment, the magnetic particles comprise iron oxide ($Fe_2O_3$ and/or $Fe_3O_4$) with diameters ranging from about 10 nanometers to about 100 micrometers. However, embodiments are contemplated in which even larger magnetic particles are used. For example, in certain embodiments, magnetic particles that are large enough to serve as a support medium for culturing cells may be utilized.

In some instances, the magnetic particles are coated with a material rendering them compatible with the microfluidics environment and allowing coupling to particular targets. Examples of coatings include polymer shells, glasses, ceramics, gels, etc. In certain embodiments, the coatings are themselves coated with a material that facilitates coupling or physical association with a target. For example, a polymer coating on a micromagnetic particle may be coated with an antibody, nucleic acid, avidin, or biotin.

One class of magnetic particles is the nanoparticles such as those available from Miltenyi Biotec Corporation of Bergisch Gladbach, Germany. These are relatively small particles made from coated single-domain iron oxide particles, typically in the range of about 10 to about 100 nanometers diameter. They are coupled to specific antibodies, nucleic acids, proteins, etc.

Another class of magnetic particles is made from magnetic nanoparticles embedded in a polymer matrix such as polystyrene. These are typically smooth and generally spherical having diameters of about 1 to about 5 micrometers. Suitable beads are available from Invitrogen Corporation, Carlsbad, Calif. These beads are also coupled to specific antibodies, nucleic acids, proteins, etc.

In some cases, the disclosed methods make use of intrinsic magnetic properties of the sample material. In such embodiments, magnetic particles need not be employed. Examples of such materials include erythrocytes, small magnetic particles for industrial applications, etc.

Electrically-Responsive Tags

Where the controllable force that is to be applied to the target comprising the tag is an electric field, a suitable tag is an electrically-responsive tag. For example, in one embodiment, a suitable tag is a charged particle which can be immobilized in a flow channel by applying a local electric field. In some cases, the disclosed methods make use of an intrinsic electrical charge of the target. In such embodiments, a charged particle need not be employed.

Suitable electrically-responsive tags are known in the art and include negatively charged polystyrene beads as demonstrated by Jonsson and Lindberg (2006) *J. Micromech. Microeng.* 16: 2116-2120.

Another type of suitable electrically-responsive tag is the dielectrophoretic tag. See for example, Hu et al, "Marker Specific Sorting of Rare Cells Using Dielectrophoresis" *Proceedings of the National Academy of Sciences*, USA, 102, 44, 15757-15761, (2005).

Acoustically-Responsive Tags

Where the controllable force that is to be applied to the target is acoustic radiation, a suitable tag is one that responds to the acoustic radiation force. For example, polystyrene and melamine micro beads have been used in the context of acoustic based microfluidic separation. See, for example, Lilliehorn et al. (2005) *Sensors and Actuators B: Chemical* 106(2): 851-858.

Condensed Light-Responsive Tags

Where the controllable force that is to be applied to the target is an electromagnetic field in the form of condensed light, e.g., laser light, a suitable tag is a particle or bead responsive to laser light.

Optical tweezers also referred to as laser tweezers, make use of an electromagnetic field in the form of condensed light. Optical tweezers are known in the art and have been used in the microfluidics context to trap and redirect microspheres as well as live cells. See, for example, Merenda et al. (2007) *Opt. Express* 15: 6075-6086.

Methods of Attachment

In some embodiments, the methods disclosed herein make use of a target to which an exogenous controllable force responsive tag has been attached. As indicated above, tag may be directly bound to the target or the tag may be indirectly bound to the target via an intermediate, e.g., a linker or a bifunctional reagent. A variety of suitable attachment techniques which may be used in connection with the methods disclosed herein is known in the art.

Figure 2:
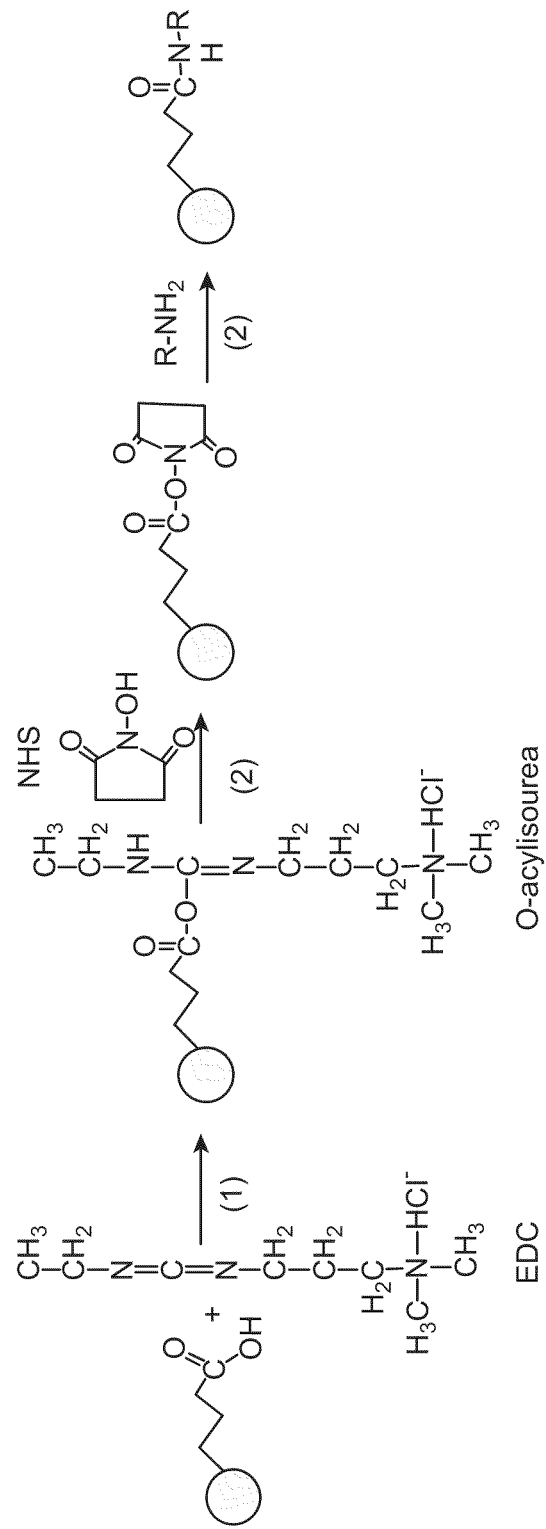
FIG. 2 is a schematic of a carbodiimide coupling method used to prepare protein-coated magnetic beads.
Figure 4:
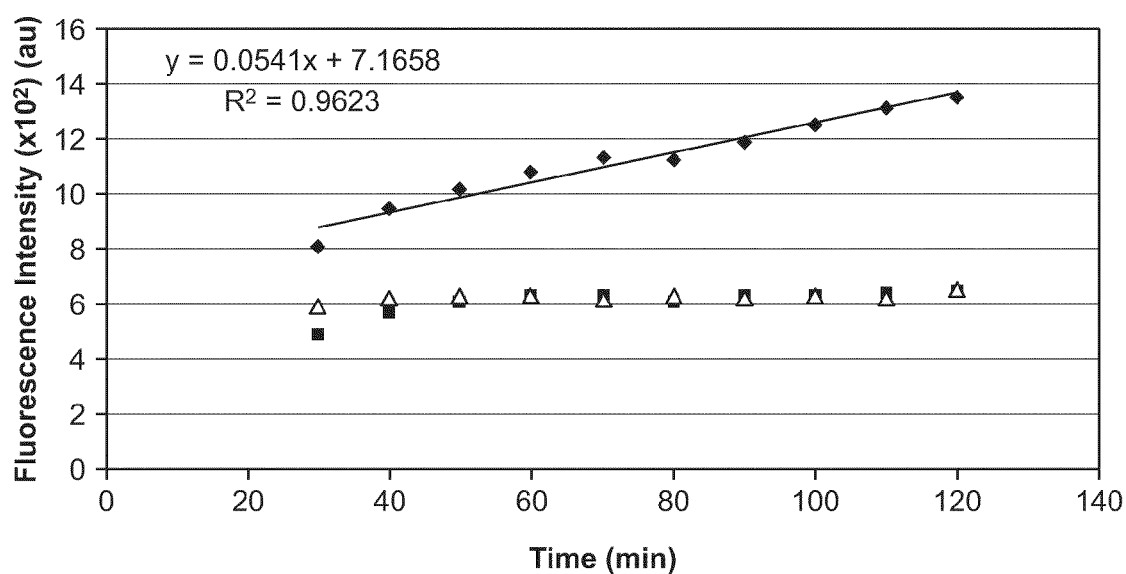
Figure 5:
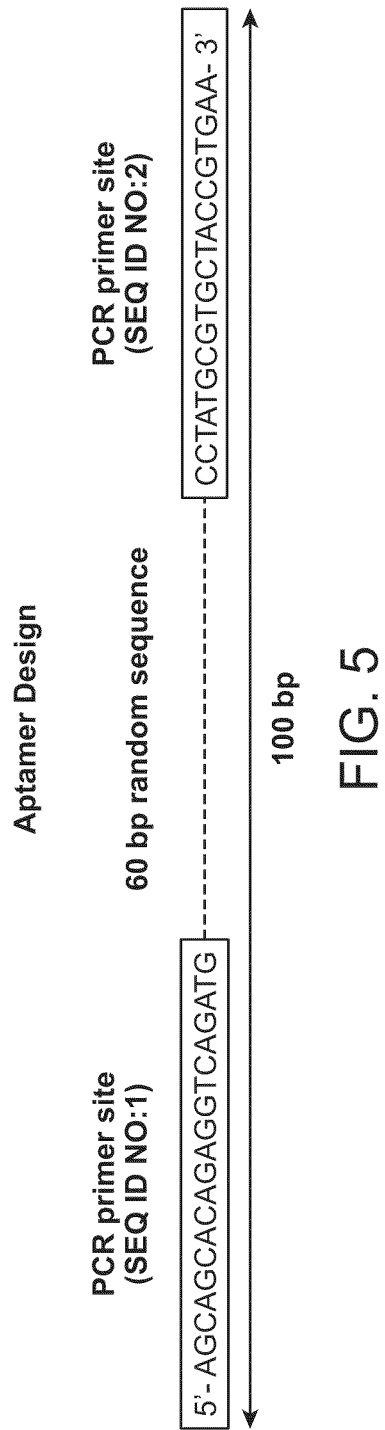
Figure 6:
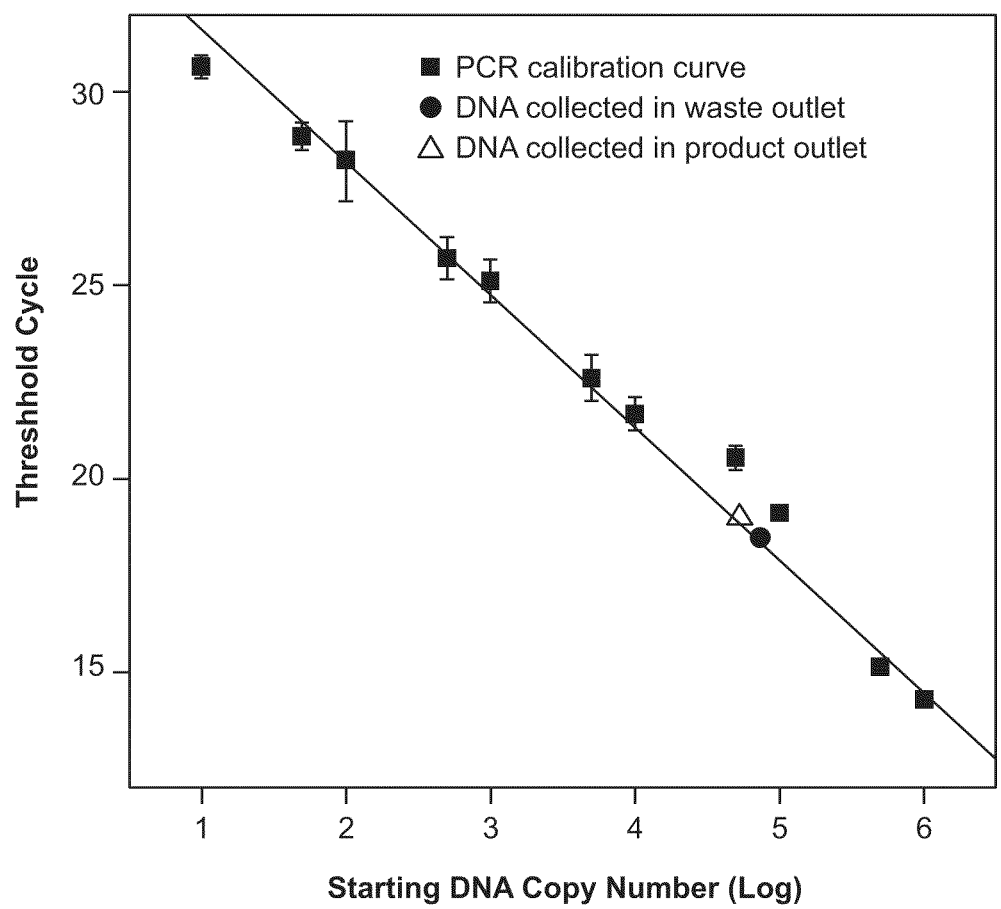
Figure 7:
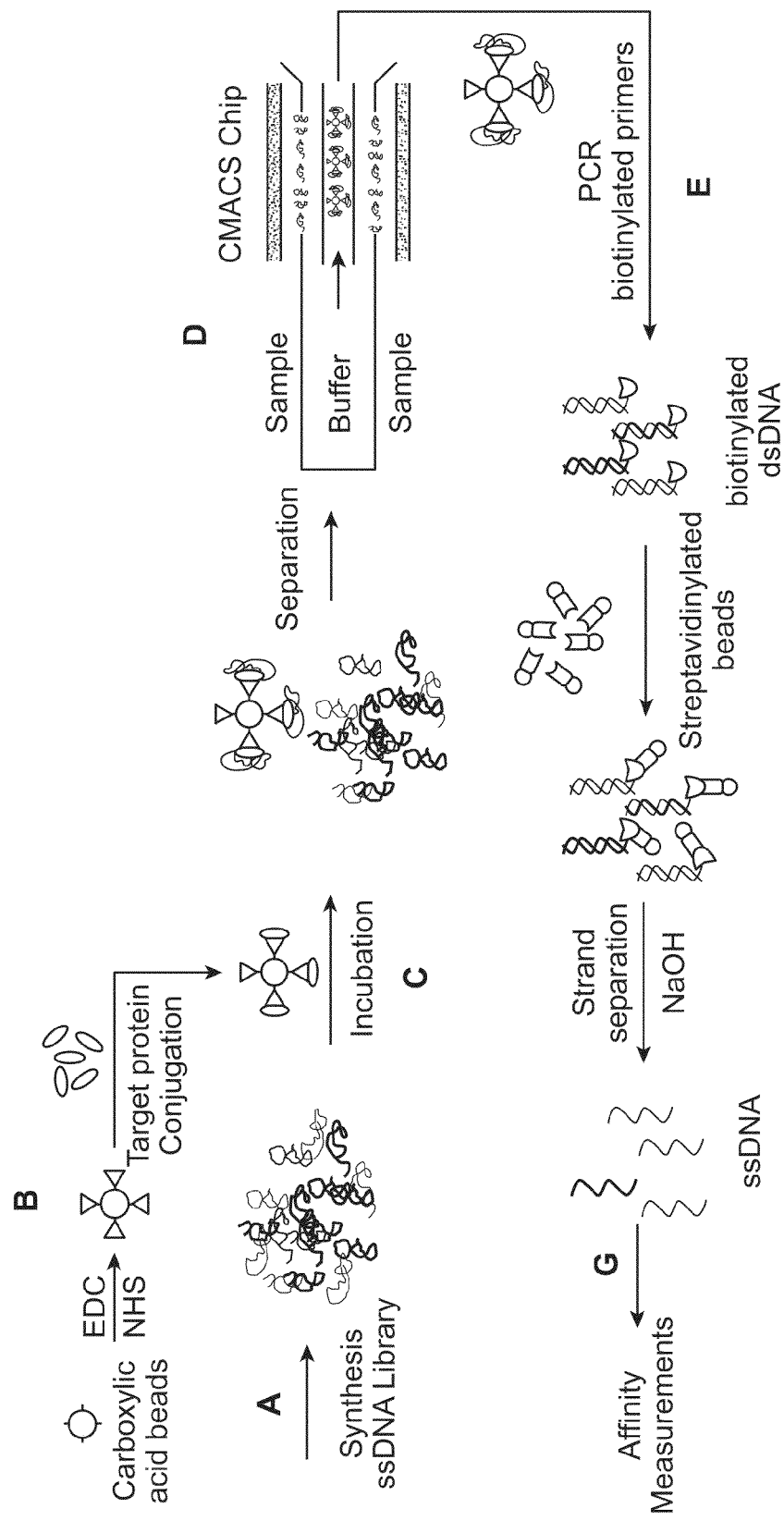

FIG. 2 provides an exemplary method for the direct attachment of a protein target to a magnetic bead using the carbodiimide coupling method. The carboxylic acid groups on magnetic beads are activated by reacting with 1-ethyl-3-(3-dimethylaminopropyl)carbodimide hydrochloride (EDC) to form the active intermediate O-acylisourea. Then this intermediate is immediately reacted with N-hydroxysuccinimide (NHS) to form a less labile active ester. The primary amino groups of the target proteins are then reacted with the NHS ester to form an amide bond with carboxylic acid group on the surface of the magnetic beads.

An example of the indirect attachment of a target molecule to a magnetic bead is provided in U.S. patent application Ser. No. 11/655,055, filed Jan. 17, 2007, and titled "SCREENING MOLECULAR LIBRARIES USING MICROFLUIDIC DEVICES," which application is incorporated by reference herein. In the referenced application, a biotin tagged target protein is attached to a magnetic microparticle via a steptavidin tag associated with the magnetic microparticle.

Additional examples include the use of tag particles coated with streptavidin and a bifunctional reagent such as a biotinylated antibody specific for the target in the sample.

The above methods may be readily adapted to the attachment of tags responsive to controllable forces other than magnetic fields. Such as, for example, the attachment of tags responsive to electric fields and/or acoustic radiation.

Controllable Forces to Facilitate Partitioning

As disclosed previously herein, a target, with respect to which a corresponding library of candidate agents is to be screened comprises a tag that responds to a controllable force; The tag is generally selected so as to be compatible with (i.e., responsive to) the particular controllable force that is to be applied to the target comprising the tag or, stated differently, the controllable force used to displace tagged targets is selected so as to be compatible with the tag. Thus, both the microfluidic device and the controllable force are selected so as to be compatible with the tag and so as to provide appropriate partition efficiency.

In some embodiments, the methods disclosed herein make use of tags which are responsive to more than one type of controllable force. For example, a particular tag may respond to both a magnetic field and an electric field. When different controllable forces are applied to the same tag, they may be applied either at the same time or alternatively one of the controllable forces may be applied to the tag prior to the application of the other controllable force.

In additional embodiments, a population of targets may comprise different target members, wherein the different target members comprise tags which are responsive to different controllable forces and further wherein the tags which are responsive to different controllable forces are not responsive to the same controllable force. For example, a first target member tag may respond exclusively to a magnetic field and a second target member tag may respond exclusively to an electric field. When different controllable forces are applied to tags responsive to different controllable forces, the forces may be applied either at the same time or alternatively one of the controllable forces may be applied to the target members prior to the application of the other controllable force.

Magnetic Fields

In one embodiment of the methods disclosed herein, the controllable force is a magnetic field, the tag is a magnetically responsive tag, and the microfluidic device is a microfluidic device which comprises a magnetic field generating element capable of displacing the tag to a second position relative to a first position by the application of the magnetic field to the tag.

A variety of microfluidic devices suitable for use in connection with the methods disclosed herein are known in the art. These include those disclosed in U.S. patent application Ser. No. 11/655,055, filed Jan. 17, 2007, and titled "SCREENING MOLECULAR LIBRARIES USING MICROFLUIDIC DEVICES," incorporated by reference previously herein; and U.S. patent application Ser. No. 11/583,989, filed Oct. 18, 2006, and titled "MICROFLUIDIC MAGNETOPHORETIC DEVICE AND METHODS FOR USING THE SAME," incorporated by reference herein. In addition, a microfluidic separation chip suitable for use with the methods described herein is described in Example 9.

In various embodiments, magnetic particles are diverted within the microfluidic device via free flow magnetophoresis. In other words, magnetic particles in a continuous flow are deflected from the direction of flow by a magnetic field or magnetic field gradient. In one example, a microfluidic device includes functionality for generating locally strong magnetic field gradients for influencing the direction of movement of the particles in the device. In certain embodiments, strips or patches or particles of materials are fixed at locations within or proximate the flow path of the library members. Specific examples are described below.

The deflection of magnetic particles can be represented as the sum of vectors for magnetically induced flow and hydrodynamic flow. The magnetically induced flow is represented by the ratio of the magnetic force exerted on a particle by the magnetic field (or field gradient) and the viscous drag force. The magnetic force is in turn proportional to the magnetic flux density and its gradient. It is also proportional to the particle volume and the difference in magnetic susceptibility between the particle and fluid. For a given magnetic field gradient and a given viscosity, the magnetic component deflection is dependent on the size and magnetic susceptibility of the particle.

In certain embodiments, the magnetic flux density applied to a microfluidic channel is between about 0.01 and about 1 T, or in certain embodiments between about 0.1 and about 0.5 T. Note that for some applications, it may be appropriate to use stronger magnetic fields such as those produced using superconducting magnets, which may produce magnetic fields in the neighborhood of about 5 T. In certain embodiments, the magnetic field gradient in regions where magnetic particles are deflected is between about 10 and about $10^6$ T/m. In a specific embodiment, the field gradient is approximately 5000 T/m within 1 micrometer from the edge of a magnetic field gradient generator.

At the point in a microfluidic flow path where separation is to occur, the magnetic field gradient should be oriented in a direction that causes deflection of the particles with respect to the flow. Thus, the magnetic field gradient will be applied in a direction that does not coincide with the direction of flow. In certain embodiments, the direction of the magnetic field gradient is perpendicular to the direction of flow. However, in other embodiments the direction of the magnetic field gradient is not perpendicular to the direction of flow.

Many different magnetic field generating mechanisms may be employed to generate a magnetic field over the displacement region of the microfluidic device. In a simplest case, a single permanent magnet may be employed. It will be positioned with respect to the flow path to provide an appropriate flux density and field gradient. Permanent magnets are made from ferromagnetic materials such as nickel, cobalt, iron, alloys of these and alloys of non-ferromagnetic materials that become ferromagnetic when combined as alloys, know as Heusler alloys (e.g., certain alloys of copper, tin, and manganese). In one specific embodiment, the permanent magnet is a cylindrical neodymium-iron-boron magnet. In another example, the magnet is an electromagnet such as a current carrying coil or a coil surrounding a paramagnetic or ferromagnetic core. In some embodiments, a controller is employed to adjust the magnetic field characteristics (the flux density, field gradient, or distribution over space) by modulating the current flowing through the coil and/or the orientation of the magnet with respect to the flowing fluid.

In some designs, a combination of magnets or magnetic field gradient generating elements is employed to generate a field of appropriate magnitude and direction. For example, one or more permanent magnets may be employed to provide an external magnetic field and current carrying conductive lines may be employed to induce a local field gradient that is superimposed on the external field. In other embodiments, "passive" elements may be employed to shape the field and produce a controlled gradient. Generally, any type of field influencing elements should be located proximate the flow path to tailor the field gradient as appropriate.

In certain embodiments, the magnetic field generating elements are provided within the sorting region channel; i.e., the fluid contacts the magnetic field generating structure. In certain embodiments, some or all of the magnetic field generating structure is embedded in channel walls (such as anywhere around the perimeter of the channel (e.g., top, bottom, left, or right for a rectangular channel)). Some embodiments permit magnetic field generating elements to be formed on top of or beneath the microfluidic cover or substrate.

Electric Fields

In one embodiment of the methods disclosed herein, the controllable force is an electric field, the tag is an electric field responsive tag, and the microfluidic device is a microfluidic device which comprises an electric field generating element capable of displacing the tag to a second position relative to a first position by the application of the electric field to the tag.

A variety of microfluidic devices suitable for use in connection with the methods disclosed herein are known in the art. These include, for example, those disclosed in Jonsson and Lindberg (2006) *J. Micromech. Microeng* 16: 2116-2120.

In one embodiment, a planer microfluidic electrocapture device is utilized which captures and concentrates beads by a local electrical field. For example, negatively charged polystyrene beads may be captured and released at an applied potential of 300V in 25 min.

Acoustic Radiation

In one embodiment of the methods disclosed herein, the controllable force is acoustic radiation, the tag is an acoustic radiation responsive tag, and the microfluidic device is a microfluidic device which comprises an acoustic radiation generating element capable of displacing the tag to a second position relative to a first position by the application of the electric field to the tag.

A variety of microfluidic devices suitable for use in connection with the methods disclosed herein are known in the art. These include, for example, those disclosed in Lilliehorn et al. (2005) *Sensors and Actuators B: Chemical* 106(2): 851-858.

In one embodiment, a suitable microfluidic device separates beads based on ultrasonic trapping of the beads using acoustic forces in standing waves. In specific embodiments, piezoelectric microtranducers may be integrated into a microfluidic channel to produce the appropriate acoustic forces.

Optical Tweezers

In one embodiment of the methods disclosed herein, the controllable force is an electromagnetic field in the form of condensed light, e.g., laser light, the tag is a particle or bead responsive to laser light and the microfluidic device is a microfluidic device which comprises a laser light generating element capable of displacing the tag to a second position relative to a first position by the application of the laser light to the tag.

Optical tweezers, also referred to as laser tweezers, make use of an electromagnetic field in the form of condensed light. Optical tweezers are known in the art and have been used in the microfluidics context to trap and redirect microspheres as well as live cells. See, for example, Merenda et al. (2007) *Opt. Express* 15: 6075-6086.

Libraries and Library Generation

Libraries can be generated so as to provide the basis for screens for binding partners of a target of interest and can be used for the identification of a variety of different binding partner pairs such as aptamer/protein, protein/protein, antibody/antigen, and nucleic acid/nucleic acid.

Generally, a molecular library is an intentionally designed collection of chemically distinct species. The library members may be small or large chemical entities of natural or synthetic origin such as chemical compounds, supermolecular assemblies, fragments, glasses, ceramics, etc. They may be organic or inorganic. In certain embodiments, they are monomers, oligomers, and/or polymers having any degree of branching. They may be expressed on a cell or virus or they may be independent entities. Because the library will normally be screened, the library designer need not know the structures and/or properties of some or all of the library members. Prior to screening, the designer typically will not know where in the library individual members are located.

As specific examples, the members of a library may be chemical compounds, mixtures of chemical compounds, biological molecules (e.g., peptides, proteins, oligonucleotides, polynucleotides (including aptamers) and combinations of any of these), viruses (e.g., bacteriophages), cells (e.g., bacteria or yeast), viruses or cells displaying peptides (e.g., antibodies), or biological materials extracted from sources such as bacteria, plants, fungi, or animal (particularly mammalian), cells or tissue or subcelluar components such as organelles (e.g., nuclei, Golgi, ribosomes, mitochondria, etc.). Note that biological molecules such as peptides, proteins, nucleic acids and the like may employ naturally occurring monomers (amino acids and nucleosides), non-naturally occurring monomers, or combinations thereof. When referring to biological polymers, it is intended to include molecules with natural and/or non-natural monomers or moieties. Those of skill in the art will readily recognize the myriad of chemical types (e.g., optical isomers, etc.) that may be employed as non-natural monomers in certain embodiments. In certain embodiments, library members may be "hybrid" molecules that include moieties (or components) from two or more different types of elements listed above. As an example, library members may include a non-amino acid small molecule group covalently attached to a short chain of peptides.

The technique employed for generating a library is of course highly dependent on the type of library under investigation. Phage and bacterial libraries for expressing genetically diverse components may be generated by well know techniques that employ controlled mutagenesis, directed evolution, etc. Peptide and oligonucleotide libraries may be produced by any suitable process for controlled combinatorial synthesis of oligomers including split and pool synthesis, array based techniques, etc.

At a minimum, a library comprises a collection of at least two different member species, but generally a library includes a number of different species. For example, a library or population typically includes at least about 100 different members. In certain embodiments, libraries include at least about 1000 different members, more typically at least about 10,000 different members. For some applications, the library includes at least about $10^6$ or more different members. However, the invention is useful in much larger libraries as well, including libraries containing at least $10^{10}$ or even $10^{14}$ or more members.

Library members may be evaluated for potential activity such as binding interaction with a defined peptide by inclusion in microfluidic screening assays described herein. In general, the methods disclosed herein can be employed to screen for one or more properties of one or more library members. If one or more of the library members is/are identified as possessing a property of interest, it is selected. Selection can include the isolation of a library member, but this is not necessary. Further, selection and screening can be, and often are, accomplished simultaneous.

Figure 3:
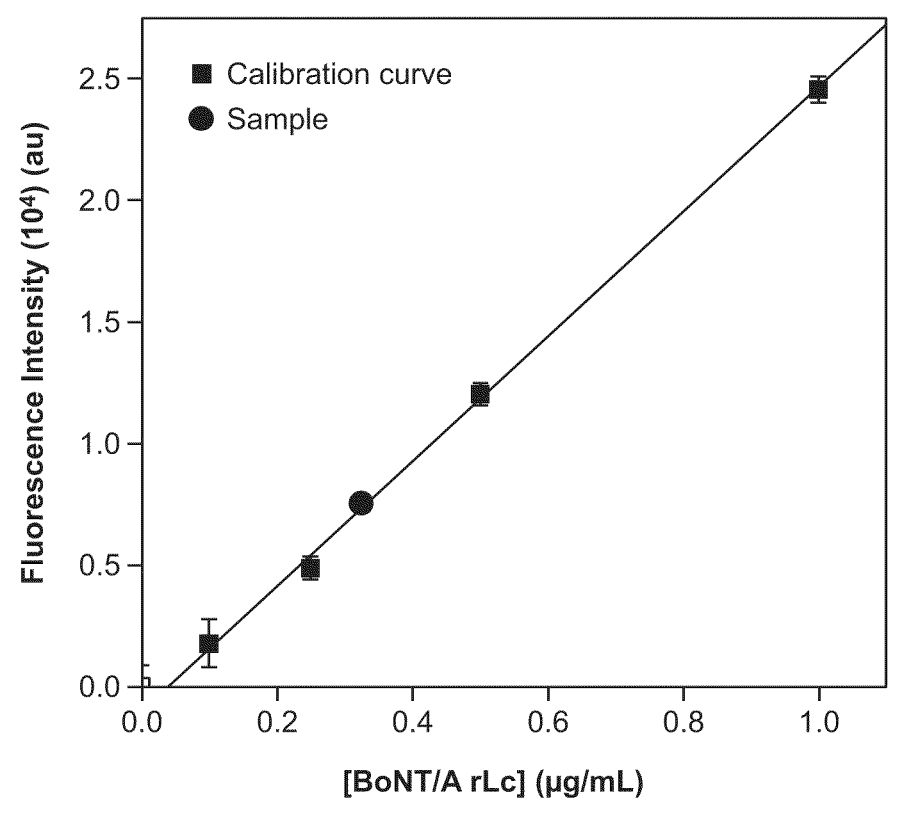

The generation of an exemplary aptamer library comprising approximately $10^{14}$ unique sequences is described in Example 2. In such an exemplary library each unique sequence is 100 bp long and contains a 60 bp internal randomized region flanked by primer sequences. The sequence of each library members from 5' to 3' may be as follows: a PCR primer site having the sequence AGCAGCACAGAG-GTCAGATG (SEQ ID NO:1) followed by the 60 bp internal randomized region followed by a PCR primer site having the sequence CCTATGCGTGCTACCGTGAA (SEQ ID NO:2). A diagram of the exemplary aptamer library design is shown in FIG. 3.

Methods of Screening to Identify from a Library a Binding Partner for a Target

The methods disclosed herein comprise a method of screening a library, the method comprising: contacting a library of candidate agents with a target in a reaction mixture under a condition of high stringency, wherein said target comprises a tag that responds to a controllable force applied to said tag; and passing the members of the library through a microfluidic device in a manner that exposes said members to said controllable force; wherein members of the library that are bound to the target are displaced relative to their unbound counterparts.

A schematic illustrating an exemplary embodiment of the screening methods disclosed herein is provided in FIG. 1. As indicated, a controllable force responsive tag is attached to a target. In certain embodiments, prior to attachment to the target, the controllable force responsive tag will be functionalized to facilitate the attachment. The target comprising the tag is then combined in a reaction mixture with a library of candidate target binding agents as indicated in (A). In certain embodiments, the initial combination of the library and the target will take place in a reaction mixture under a condition of high stringency. The reaction mixture is then passed though a microfluidic device as indicated in (B). The reaction mixture is exposed in (B) to a controllable force to which the controllable force responsive tag is responsive. In some embodiments, application of the controllable force to the reaction mixture displaces target-bound candidate target binding agents relative to their unbound counterparts. In other embodiments, application of the controllable force to the reaction mixture results in the immobilization of the target, which can facilitate exposure to different conditions of stringency as discussed below.

It should be noted that, in the methods disclosed herein, either one or both of reaction mixtures at (A) or (B) may be under a condition of high-stringency. Additionally, where the reaction mixtures at both (A) and (B) are under a condition of high stringency, the high stringency condition may be the same or different. Furthermore, by immobilizing a target in a microfluidic device by the application of a controllable force, the target can be exposed to multiple different stringency conditions such as changing salt concentration, pH, library member number or temperature such that a particular high-stringency condition or combination of high-stringency conditions of the reaction mixture changes over time.

In one aspect, the methods disclosed herein allow for the serial and/or continuous parallel introduction of a plurality of targets and/or library members into a microfluidic device. Binding interactions between the targets and library members are assessed through the application of a controllable force to targets comprising a controllable force responsive tag. This in turn facilitates the separation of target bound library members under conditions of high-stringency.

Stringency Conditions

The methods disclosed herein comprise contacting a library of candidate agents with a target in a reaction mixture under a condition of high stringency. As used herein, "a condition of high-stringency" refers to a condition that favors the specific, high affinity and/or high avidity binding of a library member with a target and under which non-specific binding as well as relatively low affinity and/or avidity binding are decreased such that candidate agents which specifically bind the target with high affinity or high avidity are separated. Furthermore, as used herein "a condition of high-stringency" includes at least one of the following: providing in the reaction mixture a total number of targets that is from at least about 3 orders of magnitude to at least about 9 orders of magnitude less than the total number of library members in the reaction mixture, a high-stringency salt concentration of the reaction mixture, a high-stringency temperature of the reaction mixture, and a high-stringency pH of the reaction mixture. Thus, in the methods disclosed herein, conditions of high-stringency result, for example, from the modulation of the relative numbers of library members to target molecules in the reaction mixture, the modulation of the temperature of the reaction mixture, the modulation of the pH of the reaction mixture, the modulation of the salt concentration of the reaction mixture, or a combination thereof.

Relative Number of Library Members to Target Molecules

Selection conditions that promote highly stringent competitive binding yield binding partners with high affinities. Such conditions may be created by exposing a very small quantity of target molecules to a library of candidate agents during incubation. Equations illustrating this concept in the context of a screen for high affinity aptamers are provided below. Within the limits of mass action kinetics, the average value of the dissociation constant ($K_d$) of the aptamers that bind to the target can be analytically expressed as equation 1:

$$\bar{K}_d = \frac{[A_T][S]}{[A_TS]} - [S] = \left[\sum_i \frac{[A_{T,i}]}{[A_T]} (K_d^{(i)} + [S])^{-1}\right]^{-1} - [S] \quad (1)$$

where [S] is the concentration of exposed unbound target; [$A_T$] is the total concentration of aptamers irrespective of binding state; [$A_TS$] is the total concentration of aptamers which are bound to the target; [$A_{T,i}$] is the total concentration of aptamers of type i, and $K_d^{(i)}$ is the dissociation constant of these aptamers. Within the limit of highly stringent competitive binding, where [S]→0, Equation 1 reduces to $$\bar{K}_{d,0} = \left[\sum_i \frac{[A_{T,i}]}{[A_T]} (K_d^{(i)})^{-1}\right]^{-1} \quad (2)$$

This result indicates that at equilibrium, the use of smallest amount of the target during the selection leads to generation of aptamers with highest affinity.

In one embodiment of the methods disclosed herein, the condition of high stringency includes providing in the reaction mixture a total number of targets that is from, at least about 3 orders of magnitude to at least about 9 orders of magnitude less than the total number of library members. For example, in specific embodiments, the total number of targets present in the reaction mixture is from at least about 3.5 to at least about 8.5, from at least about 4 to at least about 8, from at least about 4.5 to at least about 7.5, from at least about 5 to at least about 7, from at least about 5.5 to at least about 6.5, or at least about 6 orders of magnitude less than the total number of library members in the reaction mixture.

For example, where the target is a protein molecule and the library to be screened is an aptamer library, the reaction mixture may comprise a target protein concentration of about 65 pM and an aptamer library concentration of about 1 uM resulting in an aptamer library to target protein molecule ratio of about $1.5 \times 10^4$ to 1.

In some embodiments, the number of targets present in the reaction mixture will be determined by the number of tags present and the number of targets attached to each tag. In one example, a reaction mixture comprising about 1000 magnetic beads, each bead having about 100 protein molecules attached thereto, is contacted with an aptamer library of about $10^{14}$ library members, providing a ratio of aptamer library members to protein targets molecules of about $1 \times 10^9$ to 1. While in some embodiments, each tag will have the same number of targets attached, there may also be variation in the target population such that the number of targets per tag is an average for the target population as a whole.

As an additional example, where the target comprising the tag is a virus or bacterial cell, the reaction mixture may comprise about 1000 tags, with 1 virus or bacterial cell per tag. In such an example, a library of about $1 \times 10^{12}$ members would provide for a ratio of library members to targets of about $1 \times 10^9$ to 1.

Also contemplated, are reaction mixtures in which the size or structure of the target is such that the number of targets per tag is less than one. For example, where the tag is a bead and the target is a mammalian cell, there may be more than one mammalian cell attached to each bead.

Persons of ordinary skill in the art will readily appreciate that the number of tags, e.g. beads, the number of targets per tag, the number of targets and the size of the candidate agent library may be modulated either independently or in combination to arrive at a total number of targets in the reaction mixture that is from at least about 3 orders of magnitude to at least about 9 orders of magnitude less than the total number of library members in the reaction mixture.

With respect to the number of beads in the reaction mixture, it is contemplated that a range of about 100 beads/mL to about $1 \times 10^9$ beads/mL may be utilized in the methods disclosed herein. For example, the reaction mixture may comprise from about $1 \times 10^2$ beads/mL to about $1 \times 10^9$ beads/mL, from about $1 \times 10^2$ beads/mL to about $1 \times 10^8$ beads/mL, from about $1 \times 10^2$ beads/mL to about $1 \times 10^7$ beads/mL, from about $1 \times 10^2$ beads/mL to about $1 \times 10^6$ beads per mL from about $1 \times 10^2$ beads/mL to about $1 \times 10^5$ beads per mL, from about $1 \times 10^2$ beads/mL to about $1 \times 10^4$ beads per mL, or from about $1 \times 10^2$ beads/mL to about $1 \times 10^3$ beads/mL.

Generally, a tagged target is contacted with a library in a reaction mixture volume of from about 200 µl to about 500 µl. However, reaction mixture volumes outside of this range may also be utilized in connection with the methods disclosed herein. For example, reaction mixture volumes of from about 50 µL to several mL may be utilized in connection with the methods disclosed herein.

As indicated above, the number of targets in the reaction mixture may be modulated so that the total number of targets in the reaction mixture is from at least about 3 orders of magnitude to at least about 9 orders of magnitude less than the total number of library members in the reaction mixture. In some embodiments, sub-nanomolar target concentrations are used in the reaction mixture to achieve the above ratio of total number of library members to total number of targets in the reaction mixture. The term "sub-nanomolar" as used herein refers to a molar concentration greater than zero and less than or equal to 999 pico-molar.

For example, in one embodiment, the reaction mixture comprises a sub-nanomolar target protein concentration of about 65 pM and an aptamer library concentration of about 1 uM resulting in an aptamer library to target protein molecule ratio of about $1.5 \times 10^4$ to 1.

High-Stringency Temperature

As indicated above, the temperature of the reaction mixture may be modulated to produce a reaction mixture having a high-stringency temperature. The term "high-stringency temperature" refers to a reaction mixture temperature, which either alone or in combination with one or more of the additional high-stringency conditions discussed herein, favors the specific, high affinity and/or high avidity binding of a library member with a target and under which non-specific binding as well as relatively low affinity and/or avidity binding are decreased such that candidate binding agents which specifically bind the target with high affinity or high avidity are separated. Furthermore, the term "high-stringency temperature" excludes those temperatures above which or below which the structural or functional integrity of either the library members or the target is compromised. Thus, the term "high-stringency temperature" is understood with respect to the particular library members and/or targets used in the methods disclosed herein.

Persons of ordinary skill in the art can readily determine, using known assay methods and the disclosure provided herein, whether a particular reaction mixture temperature is a high-stringency temperature with respect to a particular library member and/or target. For example, the structural integrity of the library member and/or the target may be monitored over an increasing temperature range using techniques such as Nuclear Magnetic Resonance (NMR), gel electrophoresis, and antibody binding assays. The structural integrity can include, for example, the secondary and/or tertiary structure of a protein or the three dimensional structure of a non-protein molecule.

The functional integrity, e.g., the activity, of either the library member or the target may also be monitored over a range of temperatures.

For example, where either a library member or a target is an antibody, an antibody binding assay may be utilized to determine activity over an increasing temperature range.

Where either the target and/or library members comprise a protein, a high-stringency temperature will generally be from about 37° C. to about 100° C. For example, the high-stringency temperature may be from about 37° C. to about 50° C., from about 60° C. to about 80° C., from about 80° C. to about 38.5° C., from about 38.5° C. to about 39° C., from about 50° C. to about 60° C., from about 60° C. to about 70° C., from about 70° C. to about 80° C., from about 80° C. to about 90° C., or from about 90° C. to about 100° C. However, for specific proteins, a high-stringency temperature may fall outside of the above range.

Where both the target and library members comprise a nucleic acid molecule a high-stringency temperature will generally be from about 60° C. to about 100° C. or higher. For example, the high-stringency temperature may be from about 60° C. to about 70° C., from about 70° C. to about 80° C., from about 80° C. to about 90° C., or from about 90° C. to about 100° C. or higher. However, the use of temperatures outside this range is also contemplated.

For example, non-natural nucleic acids may retain activity at higher temperatures than naturally occurring nucleic acids.

High-Stringency Salt Concentration

As indicated above, the salt concentration of the reaction mixture may be modulated to produce a reaction mixture having a high-stringency salt concentration. The term "high-stringency salt concentration" refers to a reaction mixture salt concentration, which either alone or in combination with one or more of the additional high-stringency conditions discussed herein, favors the specific, high affinity and/or high avidity binding of a library member with a target and under which non-specific binding as well as relatively low affinity and/or avidity binding are decreased such that candidate binding agents which specifically bind the target with high affinity or high avidity are separated. Furthermore, the term "high-stringency salt concentration" excludes those salt concentrations above which or below which the structural or functional integrity of either the library members or the target is compromised. Thus, the term "high-stringency salt concentration" is understood with respect to the particular library members and/or targets used in the methods disclosed herein.

Persons of ordinary skill in the art can readily determine, using known assay methods and the disclosure provided herein, whether a particular reaction mixture salt concentration is a high-stringency salt concentration with respect to a particular library member and/or target. For example, the structural integrity of the library member and/or the target may be monitored over a range of concentration values using techniques such as Nuclear Magnetic Resonance (NMR), gel electrophoresis, and antibody binding assays. The structural integrity can include, for example, the secondary and/or tertiary structure of a protein or the three dimensional structure of a non-protein molecule.

The functional integrity, e.g., the activity, of either the library member or the target may also be monitored over a range of salt concentrations.

As an example, where either a library member or a target is an antibody, an antibody binding assay may be utilized to determine activity over a range of salt concentrations.

The function integrity of a library member or target in a reaction mixture having a particular salt concentration will generally vary depending on the identity library member or target. For example, while some proteins lose activity at a salt concentration of approximately 150 mM others such as streptavidin remain active up to concentrations of approximately 1M.

In some embodiments, a high-stringency salt concentration is a relatively low salt concentration. For example, where both the target and library members comprise DNA molecules a high-stringency salt concentration is generally a relatively low salt concentration, e.g., from about 5 to about 30 mM NaCl.

High-Stringency pH

As indicated above, the pH of the reaction mixture may be modulated to produce a reaction mixture having a high-stringency pH. The term "high-stringency pH" refers to a reaction mixture pH, which either alone or in combination with one or more of the additional high-stringency conditions discussed herein, favors the specific, high affinity and/or high avidity binding of a library member with a target and under which non-specific binding as well as relatively low affinity and/or avidity binding are decreased such that candidate binding agents which specifically bind the target with high affinity or high avidity are separated. Furthermore, the term "high-stringency pH" excludes those pHs above which or below which the structural or functional integrity of either the library members or the target is compromised. Thus, the term "high-stringency pH" is understood with respect to the particular library members and/or targets used in the methods disclosed herein.

Persons of ordinary skill in the art can readily determine, using known assay methods and the disclosure provided herein, whether a particular reaction mixture pH is a high-stringency pH with respect to a particular library member and/or target. For example, the structural integrity of the library member and/or the target may be monitored over a pH range using techniques such as Nuclear Magnetic Resonance (NMR), gel electrophoresis, and antibody binding assays. The structural integrity can include, for example, the secondary and/or tertiary structure of a protein or the three dimensional structure of a non-protein molecule.

The functional integrity, e.g., the activity, of either the library member or the target may also be monitored over a range of pH values.

As an example, where either a library member or a target is an antibody, an antibody binding assay may be utilized to determine activity over range of pH values.

In general, to determine a high-stringency pH, a range of pH values including values both higher and lower than the isoelectric point of the target are tested to determine whether they affect the structural and/or functional integrity of the target and/or the library members. In some embodiments, a high stringency pH is a pH that is approximately equal to the isoelectric point of the target.

Alteration of High-Stringency Conditions

The term "reaction mixture" as used herein refers to a fluid medium in which a target is contacted with or in contact with a candidate agent(s). This includes, for example, a reaction mixture in which a library of candidate target binding agents is initially contacted with a target and any subsequent wash steps designed to remove non-specific or low-affinity target binding agents. The stringency conditions of the reaction mixture can be modified so as to influence the formation of complexes between target and candidate target binding agent(s). Thus, for example, stringency conditions of a reaction mixture during initial contacting of target and a library of candidate binding agents (which may be referred to as "binding conditions") and stringency conditions of a reaction mixture during washing (referred to as "wash conditions", e.g., to disrupt complexes of an undesirably low affinity and/or deplete non-specifically bound candidate agents) may be of the same or different stringencies.

As such, in some embodiments of the methods disclosed herein, a high-stringency condition of the reaction mixture may vary during the method. For example a high-stringency condition of the reaction mixture may be modulated depending on whether the reaction mixture is one in which the library of candidate agents is initially contacted with a target or whether the reaction mixture is one designed to disrupt complexes of an undesirably low affinity and/or deplete non-specifically bound candidate agents. In specific embodiments, one or more of the high-stringency conditions discussed above may vary with respect to the reaction mixture. For example, in some embodiments, at least one of a high-stringency temperature, a high-stringency salt-concentration, a high-stringency pH, or a high-stringency relative number of library members to target molecules of the reaction mixture will differ under binding conditions as compared to wash conditions.

With respect to the modulation of high-stringency conditions, it should be noted that this modulation may be facilitated by the application of a controllable force as described herein to a tag as described herein. For example, a candidate target binding agent-target complex may be held in a specific position or location within a microfluidic device by application of the controllable force to the tagged target while a stringency condition such as the temperature, salt concentration, or pH of the reaction mixture is modulated.

Modulation of Binding Affinity

In particular embodiments, the high-stringency conditions discussed above may be modulated either separately or in combination to select for library members having a particular affinity for a particular target, as determined by $K_d$, or which fall within a desired range of affinity values for a particular target. For example, where an aptamer library is screened against a protein target, and the intended use of the aptamer is as a diagnostic tool, a high-affinity aptamer having a $K_d$ of about 10 nM to about 1 nM may be desirable. Where a therapeutic use is intended, a higher affinity binding agent may be desired, for example, in the context of a therapeutic antibody an affinity of between about 10 pM and about 100 pM may be desired and the stringency of the reaction mixture may be increased accordingly.

In some embodiments, the methods disclosed herein are designed to provide for positive selection methods. By "positive selection method(s)" is meant a library screening method wherein library members which bind to a target with a desired affinity and/or avidity, e.g., a high-affinity or avidity, are separated, identified and/or detected.

In additional embodiments, the methods disclosed herein are designed to provide for negative selection methods. By "negative selection method(s)" is meant a library screening method wherein library members which do not bind a target under a particular set of stringency conditions, e.g., high-stringency conditions, are separated, identified, and/or detected.

For example, in one embodiment, a target comprising a controllable force responsive tag is immobilized by the application of the controllable force. Library members which do not bind the immobilized target under a particular set of stringency conditions, e.g., high stringency conditions, may then be separated, identified, and/or detected.

By using positive selection methods and negative selection methods as disclosed herein, library members with desired affinities and/or avidities for a target may be identified. In addition, library members falling within a particular range of binding affinities and/or avidities may be separated, identified, and/or detected. For example, in embodiments in which a controllable force is used to hold tagged targets in place, in a microfluidic device, candidate agents can be selected so that they bind to target within a desired range of stringency, which can correlate to a desired Kd value for binding to target and or can provide for candidate agents that bind target within a desired range of Kd values. Thus, the methods disclosed herein can be modified so as to provide for screening for candidate agents that bind target under a first condition of high stringency but not at a second condition of high stringency, where the first condition is less stringent (i.e., allows for binding of lower affinity) than the second condition.

Partition Efficiency

In one embodiment, the methods disclosed herein provide a method, wherein the method comprises contacting a library of candidate target binding agents with a target in a reaction mixture under a condition of high stringency, wherein the target comprises a tag that responds to a controllable force applied to said tag, and passing the members of the library through a microfluidic device in a manner that exposes the members to the controllable force, wherein members of the library that are bound to the target are displaced relative to their unbound counterparts, and wherein the application of the controllable force provides for a partition efficiency which is greater than approximately $10^6$. For example, in some embodiments the application of the controllable force provides for a partition efficiency which is greater than approximately $10^6$, $10^7$, $10^8$, or $10^9$.

Partition Efficiency (PE) is a figure of merit that describes the efficiency of a separation method, and a high PE facilitates reduction of the number of selection rounds.

In the context of a separation method designed to separate DNA molecules which specifically bind a target protein, partition efficiency is defined as $$k_{DNA \cdot T}/k_{DNA}$$

where DNA·T is the binding complex formed between target protein and DNA. $k_{DNA \cdot T}$ and $k_{DNA}$ are collection efficiency for DNA·T and free DNA, respectively, and are calculated by the formulae:

$$k_{DNA \cdot T} = DNA \cdot T_{out}/DNA \cdot T_{in}$$

$$k_{DNA} = DNA_{out}/DNA_{in}$$

More generally, PE can be defined by the formula $$k_{CTBA \cdot T}/k_{CTBA}$$

where CTBA·T is the binding complex formed between a target and a candidate target binding agent (CTBA). $k_{CTBA \cdot T}$ and $k_{CTBA}$ are collection efficiency for CTBA·T and free CTBA, respectively, and are calculated by the formulae:

$$k_{CTBA \cdot T} = CTBA \cdot T_{out}/CTBA \cdot T_{in}$$

$$k_{CTBA} = CTBA_{out}/CTBA_{in}$$

The value of the PE is governed by the performance of the separation method to enrich for the target-candidate target binding agent complex while rejecting the free, unbound candidate target binding agents. Thus, according to the above equation, an ideal separation process would exhibit PE approaching infinity because the numerator would approach 1 as the denominator would approach 0. Traditional methods of partitioning, such as nitrocellulose membranes and affinity columns have PE typically ranging from 10 to 100. Using capillary electrophoresis (CE), PEs of greater than $10^6$, have been reported for certain targets. However, unlike CE, the methods disclosed herein do not require that the target-library member complex exhibit a shift in electrophoretic mobility. Thus, the methods disclosed herein are applicable to a wider variety of library member-target combinations. For example, the methods disclosed herein may be used in connection with small molecule targets.

Analysis of Partitioned Particles

The methods disclosed herein also provide for the analysis of the target bound members displaced relative to their unbound counterparts as a result of the methods disclosed herein. Analysis may include, for example the amplification, separation, and/or detection of the target bound members displaced relative to their unbound counterparts.

Amplification

In one embodiment, a method disclosed herein comprises contacting a library of candidate target binding agents with a target in a reaction mixture under a condition of high stringency, wherein said target comprises a tag that responds to a controllable force applied to said tag, and passing the members of the library through a microfluidic device in a manner that exposes said members to said controllable force, wherein members of the library that are bound to the target are displaced relative to their unbound counterparts, and further comprises amplifying the members of the library that are displaced relative to their unbound counterparts.

Amplification is primarily relevant when particular genetic material is to be analyzed or detected. PCR or other known amplification techniques may be appropriate for this purpose. For example, where the library is an aptamer or other nucleic acid library the direct amplification of target-bound aptamers may be conducted using HotStart PCR as described in Example 4.

Separation

Separation of the target bound members displaced relative to their unbound counterparts may include, for example, separation techniques which make use of an affinity tag present on the target bound library members. Separation can also refer to the separation of a library member from its bound target. Many such methods are known in the art. For example, separation steps may utilize affinity columns, membranes, electrophoresis, chromatography, surface plasmon resonance and other analytical separation methods.

Detection

Detection of the target bound members displaced relative to their unbound counterparts may include, for example, detecting the presence of the target or library member via a microscopy, a fluorescent signature, a radioactive signal, etc. Either one or both of the target and the library member may be detectably labeled. Examples of detection processes suitable for use with the invention include continuous flow processes such as various cell counting techniques or immobilization techniques such as microarray analysis.

As used herein, the terms "label" and "detectable label" refer to a molecule capable of detection, including, but not limited to, radioactive isotopes, fluorescers, chemiluminescers, chromophores, enzymes, enzyme substrates, enzyme cofactors, enzyme inhibitors, chromophores, dyes, metal ions, metal sols, ligands (e.g., biotin, avidin, strepavidin or haptens) and the like. The term "fluorescer" refers to a substance or a portion thereof which is capable of exhibiting fluorescence in the detectable range. Exemplary detectable moieties suitable for use as detectabe labels include affinity tags and fluorescent proteins.

The term "affinity tag" is used herein to denote a peptide segment that can be attached to a target that can be detected using a molecule that binds the affinity tag and provides a detectable signal (e.g., a fluorescent compound or protein). In principal, any peptide or protein for which an antibody or other specific binding agent is available can be used as an affinity tag. Exemplary affinity tags suitable for use include, but are not limited to, a monocytic adaptor protein (MONA) binding peptide, a T7 binding peptide, a streptavidin binding peptide, a polyhistidine tract, protein A (Nilsson et al., EMBO J. 4:1075 (1985); Nilsson et al., Methods Enzymol. 198:3 (1991)), glutathione S transferase (Smith and Johnson, Gene 67:31 (1988)), Glu-Glu affinity tag (Grussenmeyer et al., Proc. Natl. Acad. Sci. USA 82:7952 (1985)), substance P, FLAG peptide (Hopp et al., Biotechnology 6:1204 (1988)), or other antigenic epitope or binding domain. See, in general, Ford et al., Protein Expression and Purification 2:95 (1991). DNA molecules encoding affinity tags are available from commercial suppliers (e.g., Pharmacia Biotech, Piscataway, N.J.).

Any fluorescent polypeptide (also referred to herein as a fluorescent label) well known in the art is suitable for use as a detectable moiety or with an affinity tag of the peptide display scaffolds described herein. A suitable fluorescent polypeptide will be one that can be expressed in a desired host cell, such as a bacterial cell or a mammalian cell, and will readily provide a detectable signal that can be assessed qualitatively (positive/negative) and quantitatively (comparative degree of fluorescence). Exemplary fluorescent polypeptides include, but are not limited to, yellow fluorescent protein (YFP), cyan fluorescent protein (CFP), GFP, mRFP, RFP (tdimer2), HCRED, etc., or any mutant (e.g., fluorescent proteins modified to provide for enhanced fluorescence or a shifted emission spectrum), analog, or derivative thereof. Further suitable fluorescent polypeptides, as well as specific examples of those listed herein, are provided in the art and are well known.

Biotin-based labels also find use in the methods disclosed herein. Biotinylation of target molecules, library molecules and substrates is well known, for example, a large number of biotinylation agents are known, including amine-reactive and thiol-reactive agents, for the biotinylation of proteins, nucleic acids, carbohydrates, carboxylic acids; see, e.g., chapter 4, Molecular Probes Catalog, Haugland, 6th Ed. 1996, hereby incorporated by reference. A biotinylated substrate can be detected by binding of a detectably labeled biotin binding partner, such as avidin or streptavidin. Similarly, a large number of haptenylation reagents are also known.

Kits and Systems
Kits

Also provided by the subject invention are kits for use in practicing the methods disclose herein. The subject kits typically include a high-stringency reaction mixture, as described above, or at least components for making such reaction mixture, e.g., a reaction mixture having a high-stringency salt concentration, high-stringency pH and/or a total number of targets that is from at least about 3 orders of magnitude to at least about 9 orders of magnitude less than the total number of library members in the reaction mixture. In addition, the subject kits may further include a target comprising a controllable force responsive tag, as described above. The subject kits may also include a microfluidic device comprising a controllable force generating element, as described above. Also of interest are kits that include one or more label reagents for producing labeled target and/or library members. Furthermore, the kits may include one or more positive or negative controls, e.g., pre-labeled target binding member known to bind a particular target with high affinity, etc.

The various components of the kit may be present in separate containers or certain compatible components may be precombined into a single container, as desired.

In addition to the above components, the subject kits will further include instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another means would be a computer readable medium, e.g., diskette, CD, etc., on which the information has been recorded. Yet another means that may be present is a website address which may be used via the internet to access the information at a removed site. Any convenient means may be present in the kits.

Systems

Also provided are systems for use practicing the subject methods. The subject systems include at least the high-stringency reaction mixture described above, and a detector device for detecting target bound library members. The subject systems may also include additional components necessary for practicing a given embodiment of the subject methods, e.g., buffers, enzymes, and primers for use in the PCR amplification of target bound library members as described above.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); and the like.

Example 1

Preparation of Target Molecules Bound to a Magnetically Responsive Tag

In order to ensure highly competitive aptamer-target binding conditions, the number of target proteins bound to carboxylic acid-functionalized magnetic beads was controlled via carbodiimide coupling chemistry. In this coupling reaction, carboxylic acids are activated by the formation of a reactive N-hydroxysuccinimide (NHS) ester at low pH, proceeding through the formation of a less stable ester with 1-[3-(dimethylamino)propyl]-3-ethylcarbodiimide (EDC). The activated esters are then exposed to amino groups in the target protein at a higher pH to accelerate deprotonation of the amine, which then reacts with the NHS-ester to yield a stable amide bond.

Materials and Methods

Target protein molecules (Botulinum Neurotoxin Type A Light Chain) (BoNT/A-rLc) were covalently bound to magnetic Dynabeads® M-270 using a carbodiimide coupling method. Specifically, 100 µL of Dynabeads® M-270 carboxylic acid-terminated magnetic beads (Invitrogen Dynal AS, Oslo, Norway) were washed twice with 100 µL of 25 mM 2-(N-morpholino)ethane sulfonic acid (MES) (pH 5.0) for 10 minutes. 50 mg/mL 1-ethyl-3-(3-dimethylaminopropyl)carbodiimide hydrochloride (EDC) and 50 mg/mL N-hydroxysuccinimide (NHS) were freshly prepared in cold 25 mM MES (pH 5.0). 50 µL of EDC solution and 50 µL of NHS solution were added to the washed beads, which were mixed well and then incubated with slow rotation at room temperature for 30 min.

After incubation, the activated beads were washed 4 times in a Magnetic Particle Concentrator (MPC) separator (Invitrogen Dynal AS, Oslo, Norway) for 2 min and the supernatant was removed. Solution containing 1 µg of target protein BoNT/A-rLc (Botulinum Neurotoxin Type A Light Chain) (List Biological Laboratories, INC., Campbell, Calif.) in reconstitution buffer (List Biological Laboratories, INC., Campbell, Calif.) and 25 mM MES (pH 5.0) was added to the beads to a final volume of 100 µL. This mixture was then incubated at room temperature for 2 hr with slow rotation.

After incubation, the unbound BoNT/A-rLc was removed by MPC separator. The protein-coated beads were then incubated with 50 mM Tris (pH 7.4) for 15 min to quench the unreacted carboxylic acid groups, then washed 4 times with 100 µL PBS buffer containing 0.1% Tween-20 and finally stored at 4° C. in the same buffer.

The amount of BoNT/A-rLc immobilized on the beads was measured using NanoOrange® Protein Quantification Kit (Molecular Probes, Eugene, Oreg.). Fluorescence measurements were performed in a 96-well black microplate using a microplate reader (TECAN microplate reader). The excitation wavelength was 485 nm and emission was 590 nm.

To determine whether the target (BoNT/A-rLc) immobilized onto the beads maintained its activity, a SNAPtide® assay was performed as follows. Each SNAPtide® assay containing 8 µM SNAPtide® substrate in 100 µL 20 mM HEPES buffer, pH8.0, was run at 37° C. $4 \times 10^7$ beads with or without BoNT. Fluorescence measurements were performed in 96-well black microplate (Microfluor™ 2 from Thermo Lab) using a Tecan® microplate reader. Excitation wavelength was 490 nm and emission was 523 nm.

Results

FIG. 3 shows a BoNT/A-rLc standard curve (black line) generated by subtracting the absolute fluorescence value of a blank sample (0 μg/mL) from that of each experimental sample. The concentration of BoNT/A-rLc in 18 μL of the supernatant as measured following dilution to a final volume of 357 μL was 0.32±0.04 μg/mL (●). The calculated amount of BoNT/A-rLc on beads was 3.2±0.8 μg/mL or 65±17 nM (bead concentration was $2\times10^9$ beads/mL). The standard deviation was calculated from three measurements of the three replicates. The number of target molecules per bead was $\sim2\times10^4$.

FIG. 4 shows the results of activity assays for bead-BoNT (♦) via SNAPtide® assay from List Biological Laboratories, INC. (Campbell, Calif.). Two controls were included into this assay: bare carboxylic acid Dynabeads® M-270 (■) and the blank sample (▲). A close to linear fluorescence intensity increase over time for the target coated beads clearly demonstrated the enzyme activity of the BoNT/A-rLc was preserved after coupling to the carboxylic acid beads.

Example 2

Aptamer Library Design

An exemplary library of candidate target binding agents for use in disclosed screening methods was prepared as follows. An aptamer library was synthesized which contained $\sim10^{14}$ unique sequences, each 100 bp long and containing a 60 bp internal randomized region flanked by primer sequences. The sequence of each library members from 5' to 3' was as follows: a PCR primer site having the sequence AGCAGCACAGAGGTCAGATG (SEQ ID NO:1) followed by the 60 bp internal randomized region followed by a PCR primer site having the sequence CCTATGCGTGCTACCGTGAA (SEQ ID NO:2). A diagram of the exemplary aptamer library design is shown in FIG. 5.

Example 3

DNA Separation Performance of an Exemplary CMACS Device

Partition Efficiency (PE) is commonly used as a benchmark for molecular separation methods.

Materials and Methods

The partition efficiency of a Continuous Flow-Magnetic Actuated Cell Sorter (CMACS) was determined by comparison to a real-time PCR calibration curve. A real-time PCR standard calibration curve was first generated using a set of ssDNA molecules, each molecule having the same sequence. This calibration curve was then used to measure the amount of DNA collected in the product channel and waste channel. A CMACS ssDNA separation experiment was also conducted using the same ssDNA as used in the calibration experiments.

For the CMACS device, PE was defined as the ratio of DNA collected through the Waste outlet compared to those collected through the Product outlet, when a standard number of beads are processed without any immobilized target proteins (to account for any non-specially bound DNA to the beads). Thus larger PE values indicate higher purity separation. The PE of CMACS was measured by quantifying the amount of DNA in both outlets via quantitative real-time PCR. The CMACS device was operated under typical conditions, in which buffer was pumped at 5 mL/hr and samples containing 1 μM ssDNA and magnetic beads ($2\times10^6$ beads/mL) were pumped at 1 mL/hr.

Results

FIG. 6 shows the real time PCR calibration curve for partition efficiency measurements (■). PCR calibration reactions were conducted at 20 μL scale with three replicates for each template concentration using iQ SYBR Green Supermix from Bio-rad. Forward and reversed primers were at 500 nM. 100 bp ssDNA (5'-AGCAGCACAGAGGTCAGATGCTTTGGAGACAGTCCGTGGTAGGGCAGGTTGGGGTGACTTCGGAAGAAGCGAGACGGTCCTATGCGTGCTACCGTGAA-3' (SEQ ID NO:3)) was used as the template for both calibration curve and partition efficiency measurements. The primer sites are shown in bold. The partition efficiency (PE) of the CMACS chip was calculated by dividing the DNA copy number in the waste channel (●) by the copy number in the product channel (▲). The collection in the waste channel was diluted $10^6$ to fall into the calibration range.

Using the above method, the PE for the Continuous Flow-Magnetic Actuated Cell Sorter (CMACS) microfluidic system was determined to be $1.4\pm0.6\times10^6$. This partition efficiency is significantly greater than that achieved by previous aptamer selection methods such as traditional Systematic Evolution of Ligands through Exponential enrichment (SELEX) utilizing nitrocellulose filters or affinity columns, which exhibit a partition efficiency range of about 10-100, and is comparable to the PE of Nonequilibrium Capillary Electrophoresis of Equilibrium Mixtures (NCEEM), which has a partition efficiency of greater than $10^6$.

This high-purity molecular separation is facilitated by the multiple-stream laminar flow architecture of the CMACS device. More specifically, by independently controlling the flow rate of the sample and buffer streams, the distance between the Product outlet and the interface of the two streams (denoted by m in FIG. 9, c (III)) can be regulated such that m (>300 μm) is significantly larger than the diffusion length of unbound DNA ($L_{diff}\sim4.2$ μm). Here $L_{diff}$ is approximately $\sqrt{D_{DNA} t_{residence}}$, where $D_{DNA}$ is the diffusivity of the unbound DNA, and residence is the time for an average molecule to travel through the device. In this way, the unbound DNA is effectively prevented from diffusing into the Product outlet and a high PE is thereby achieved reproducibly, without any washing steps.

Example 4

Pilot Polymerase Chain Reaction (PCR)

A pilot PCR was conducted to determine the optimized cycle number for PCR amplification of the selected aptamer library. A PCR mixture containing 25 μL HotStarTaq Master Mix (Qiagen, Hilden, Germany), 0.25 μL 100 μM forward primer (FP), 0.25 μL 100 μM biotinylated reverse primer (RP-Biotin), and 24.5 μL of DNA sample collected from CMACS was prepared. After preheating at 95° C. for 15 min, samples were subjected to 35 thermal cycles of heating at 95°

C. for 30 s, annealing at 56° C. for 30 s and extension at 72° C. for 30 s. 5 μL of PCR reaction mixture were removed during the elongation step at specific cycles and stored on ice until all samples were collected. The optimized PCR cycle number for amplification of the selected library was determined by resolving PCR products on a 10% PAGE-TBE gel.

Example 5

Isolation of High-Affinity Aptamers

The following steps were utilized to isolate aptamers having a high affinity for BoNT/A-rLc:

An initial aptamer library of ~$10^{14}$ unique sequences was synthesized by standard techniques. Each aptamer of the library was 100 bp long and contained a 60 bp internal randomized region flanked by primer sequences as shown in FIG. 3.

500 picomoles of ssDNA library (~$10^{14}$ copies) in 494.5 μL 1× binding buffer (20 mM HEPES, 150 mM NaCl, 2 mM KCl, 2 mM $MgCl_2$, 2 mM $CaCl_2$, pH 7.4) without glycerol were heated at 95° C. for 10 min, rapidly cooled for 5 min in an ice bath and then incubated for another 5 min at room temperature. 0.5 μL of BoNT/A-rLc-coated magnetic beads (~$2\times10^{10}$ BoNT/A-rLc molecules on $1\times10^6$ beads) were then added and incubated with the library for 2.5 hr at room temperature. After incubation, 50 μL of glycerol was added into the mixture in order to prevent beads precipitation during separation step, which was then separated in the CMACS device.

The sample was then separated in the Continuous-flow Magnetic Activated Chip-based Separation (CMACS) device (FIG. 7, Step D) to purify the DNA bound to the BoNT/A-rLc-coated beads. The volumetric throughput was 1 mL/hr, and thus it took approximately 30 minutes to complete the separation. The aptamers bound to target-coated beads were collected at the product outlet in a final volume of approximately 680 μL (FIG. 7, Step D), and were amplified via polymerase chain reaction (PCR) as described in Example 6 below (see FIG. 7, Step E). The unbound oligonucleotides were eluted through the Waste outlet of the device. Following PCR, fluorescently-labeled single-stranded DNAs were isolated as described in Example 6 below (see FIG. 7, Step F).

Example 6

Single-Stranded (ss) DNA Generation

The collected aptamer pool was amplified via PCR at the optimized cycle number determined by the pilot PCR described in Example 4, using the forward primer (either FP, FP-Alexa or FP-$A_{24}$) and biotinylated reverse primer (RP-Biotin). The biotin-labeled double-stranded (ds) PCR product was incubated with Dynabeads® MyOne™ Streptavidin $C_1$ (Invitrogen Dynal AS, Oslo, Norway) for 2 hr at room temperature to separate the ds-DNA from the PCR reaction mixture, according to the manufacturer's protocol. Single-stranded DNA was then generated in solution by incubating the beads with 15 mM NaOH for 4 min at room temperature. The supernatant was collected and neutralized with 1 M HCl. The amount of single-stranded DNA in solution was determined at 260 nm via UV-vis absorption. The purity of the single-stranded DNA was examined on a 10% PAGE-TBE Urea gel.

Example 7

Affinities of Aptamers Generated in a Single Round of Selection

After a single round of microfluidic separation (as described in Example 5), PCR amplification and single-strand DNA generation (as described in Example 6), the bulk binding affinity of the enriched aptamer pool was subsequently measured via a fluorescence binding assay.

Materials and Methods

The dissociation constant ($K_d$) of the amplified aptamer pool was determined optically. The Alexa 488N-labeled aptamer pool was diluted to several different concentrations (from 0 to 200 nM) in 100 μL of 1× binding buffer; these dilutions were heated at 90° C. for 10 min, rapidly cooled down to 0° C. in an ice bath, and then incubated for another 10 min at room temperature. $1\times10^8$ BoNT/A-rLc coated beads were washed in 1× binding buffer and re-suspended in the heat-treated aptamer solution, and then incubated at room temperature for 1 hr. After incubation, unbound aptamers were removed by washing four times with 1×PBS buffer containing 0.05% Tween-20. The bound aptamers were then eluted into 100 μL 1×PBS buffer by heating the aptamer-bound protein-coated beads at 95° C. for 8 min with shaking. The quantity of aptamers eluted from the beads was subsequently determined by fluorescence measurements (TECAN microplate reader) and calculated from a calibration curve. The amount of DNA eluted from the beads was plotted as a function of aptamer concentration (FIG. 8). The dissociation constant $K_d$ was calculated by fitting to the kinetic model, assuming Langmuir binding (1:1).

Results

The initial library showed no significant binding affinity to the target protein (FIG. 8, ●). In contrast, assuming a 1:1 Langmuir binding model, the dissociation constant ($K_d$) of the enriched aptamer pool after a single round of M-SELEX was 33±8 nM (FIG. 8, ■), and it showed negligible affinity to magnetic beads without the target (FIG. 8, ▲). Furthermore, the total amount of aptamers eluted from the beads (~6 nM) was closely matched to the estimated amount of bead-conjugated target used in this assay (7±2 nM), suggesting that the binding is indeed specific to BoNT/A-rLc.

These results represent an improvement over conventional SELEX methods which typically require multiple rounds of selection due to the non-stringent selection conditions and low partition efficiencies. The M-SELEX process, makes use of higher molar ratios between the DNA library and protein targets ($R_{library/target}$) in order to achieve higher efficiency selection. For example, in conventional SELEX, $R_{library/target}$ ranges between 10 and 1000. In this M-SELEX experiment a $R_{library/target}$ value of $1\times10^6$ was used, which yielded aptamers with low nM affinity after a single round of selection. In contrast, when two rounds of selection were performed against the same target under otherwise similar conditions at a ~6500-fold lower stringency ($R_{library/target}$=~150), the resulting aptamers showed significantly lower binding affinities for the protein target (FIG. 8 (▼)).

The M-SELEX method also represents an improvement over electrophoretic separation methods such as capillary electrophoresis (CE) since such methods are limited to targets that exhibit significant mobility shift upon binding to the aptamers. CE typically requires careful tuning depending on the specific $\mu_e$ of each target-aptamer complex, and is thus not suitable for targets that do not cause significant changes in $\mu_e$, such as small molecules and cell surfaces. In comparison, M-SELEX is advantageous because it works equally well for any bead-bound targets; once the target is immobilized on the magnetic beads, the separation process and parameters (e.g., magnetic actuation and flow rates) remain the same, and do not require any tuning.

Example: 8

Cloning, Sequencing and Analysis of Selected Aptamers

Materials and Methods

Figure 9:
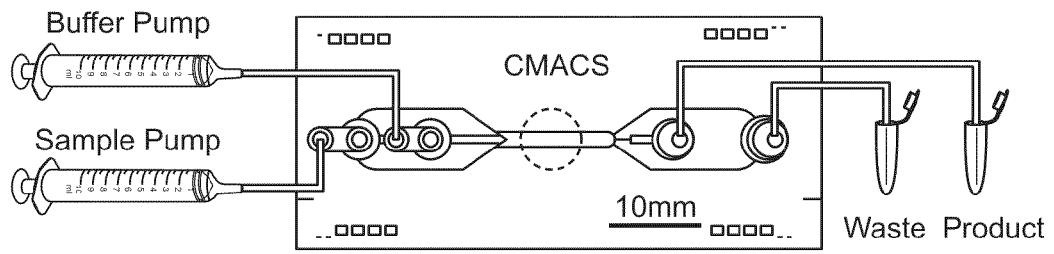
Figure 9:
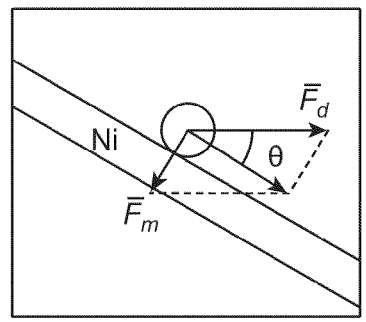
Figure 9:
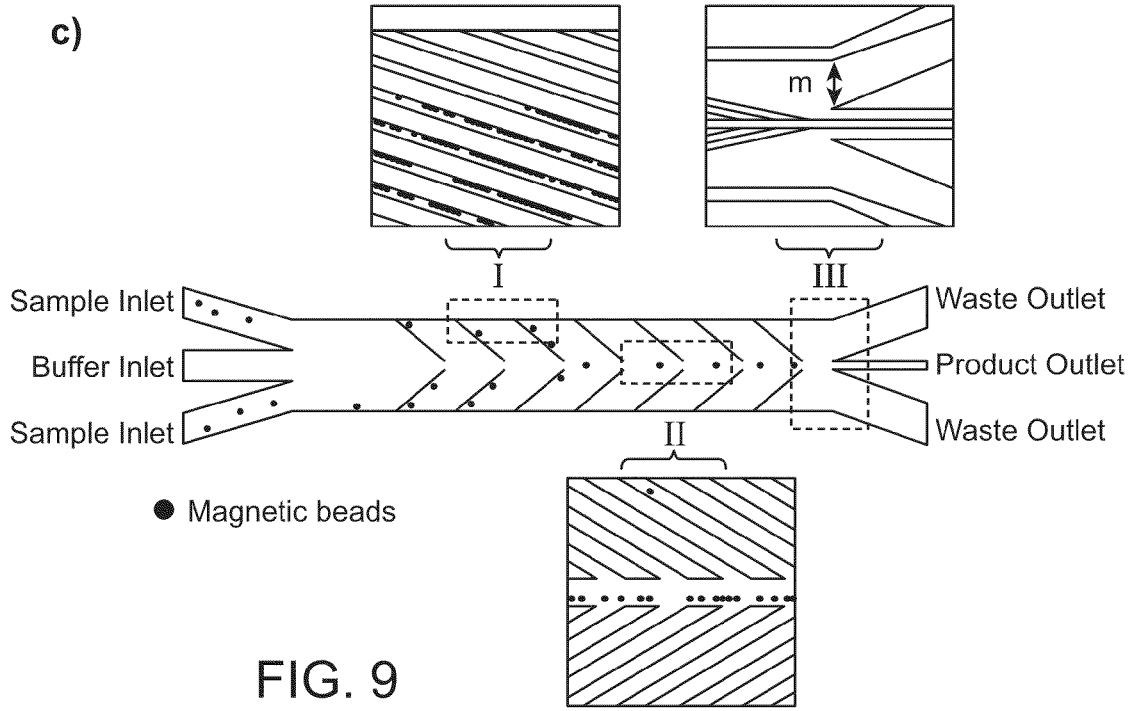
Figure 10:
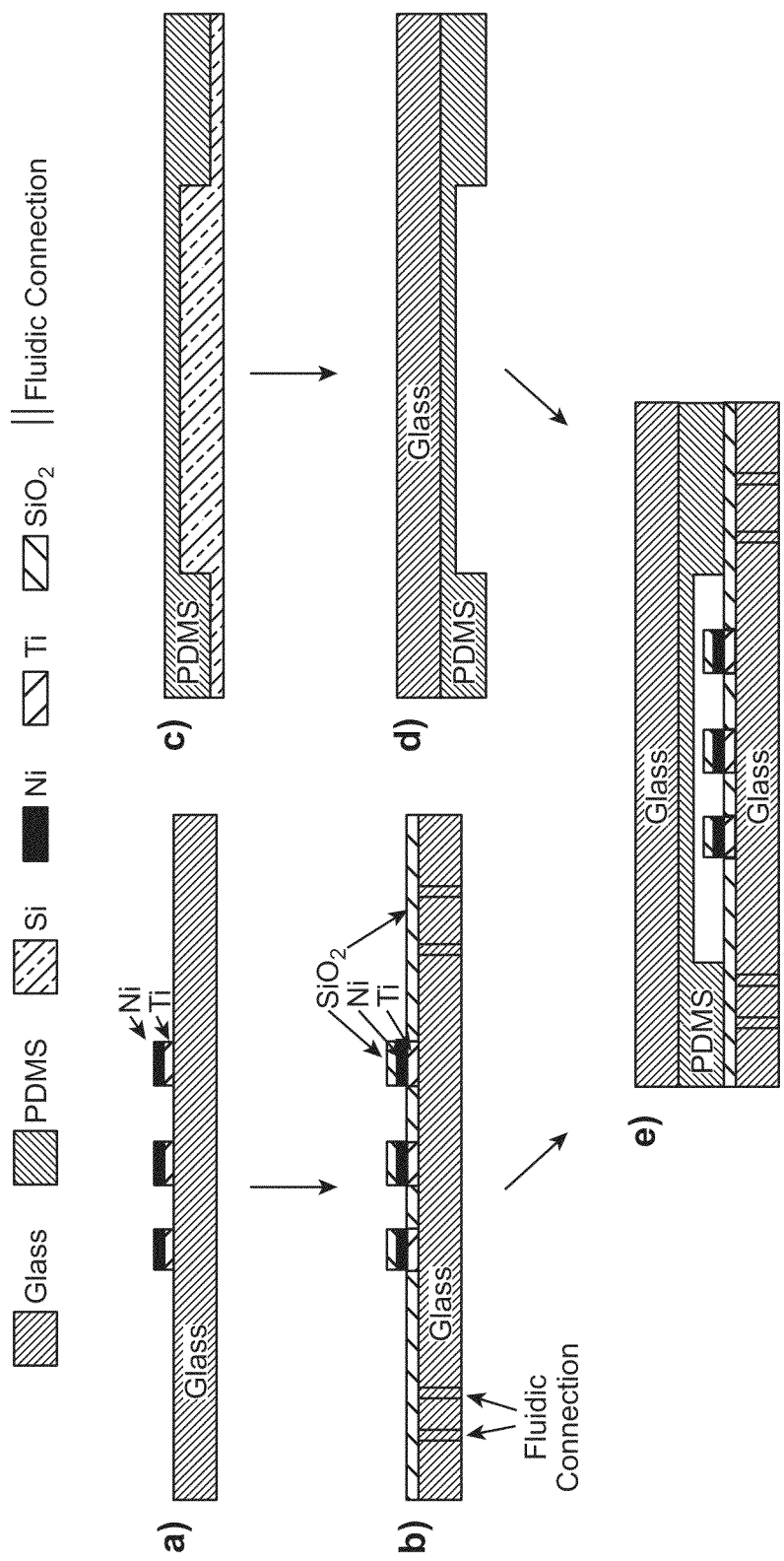

1% of the collected aptamer pool was PCR amplified with unlabeled forward and reversed primers at the cycle number determined by the pilot PCR (Example 4). The PCR products were purified using the MiniElute® PCR Purification Kit (Qiagen, Hilden, Germany) and cloned with the TOPO TA Cloning kit (Invitrogen, Carlsbad, Calif.). 15 colonies were randomly picked, purified and sequenced, and four of the isolated sequences were synthesized and measured for their binding affinity to BoNT/A-rLc. Plasmids were purified using the QIAprep Spin Miniprep Kit from Qiagen and sequenced at the UC Berkeley DNA Sequencing Facility. Secondary structure analysis was performed with mfold software available on the web site located by placing "www" in front of ".idtdna.com/Scitools/Applications/mFold/)".

$K_d$ was measured for the four selected aptamers using surface plasmon resonance (SPR) (BIAcore 3000, GE Healthcare, Waukesha, Wis.). First, approximately 1000 RU of biotinylated oligo$(dT)_{24}$ were attached to the reference and sample channels of the streptavidin (SA) coated SPR chip surface by injecting 10 μL 1 μM oligo$(dT)_{24}$ solution into streptavidin-biotin binding buffer (1 M NaCl, 5 mM Tris-HCl, 0.5 mM EDTA, pH 7.5) at a flow rate of 5 μL/min. The free binding sites were subsequently blocked with biotinylated polyethylene glycol (PEG). Synthesized aptamers, modified with 24-mer poly(A) oligonucleotides at the 5' end, were injected into the sample channel at a flow rate of 20 μL/min for 2.5 min to hybridize with the complementary biotinylated oligo$(dT)_{24}$ on the SA chip, resulting in an ~700 RU increase. A spacer was included between the poly(A) and the aptamer sequence to avoid overlapping the hybridizing region with the aptamer binding site. Similarly, the initial library was immobilized on the reference channel as a negative control, with a similar RU increase. To improve the DNA hybridization efficiency, samples were pretreated under basic conditions to destroy their secondary structures. More specifically, DNAs were mixed with 20% formamide, 0.3 M NaOH in 1×PBS buffer to a final concentration of 50 nM and incubated at 42° C. for 30 min. After incubation, the solution was neutralized with 1 M HCl. Finally, BoNT/A-rLc in 1× binding buffer from low to high concentrations (5-200 nM) was sequentially injected into both the reference and sample flow cells at a rate of 20 μL/min for 3 min. The dissociation constant $K_d$ was calculated by fitting to the Langmuir kinetic model.

Results

The sequences of the core regions of the four selected aptamers and their respective dissociation constants are provided below in Table 1. The dissociation constants ranged from 34 to 86 nM, which is consistent with the average $K_d$ obtained from the selected aptamer pool. Using mfold software, the secondary structure of these aptamers was modeled and it was found that the consensus regions for the four sequences form small protruding loops and stems. Without being bound by any particular theory, it is presumed that these small protruding loops and stems make the aptamers more accessible to target binding.

TABLE 1

| Aptamer ID | Core region of the selected aptamers | KD[nM] |
|---|---|---|
| a | TCTTTCATACCGAGGTTGATCCAGTAGTATTC TTATCTAATTTGTTTTGTTCGTATGTGC (SEQ ID NO:4) | 65 |
| b | TGGTCTTGTCTTTCATTCCAGGTGGCGAGTCA AATCGATACTGATCCGCTGACACAGGAT (SEQ ID NO:5) | 86 |
| c | CTTGAGTGTCATGGACGTTCCGGTCTTGGGCG GGATATTTGTTTGTTTTCTGCCTATGTT (SEQ ID NO:6) | 34 |
| d | TCAGATGGCCGGACTCAGGCACTAGACCACTA TGCTTCCGTTGCCATTCATCGGCACGT (SEQ ID NO:7) | 53 |

Example: 9

Design and Fabrication of an Exemplary Continuous Flow-Magnetic Actuated Cell Sorter (CMACS) Device The CMACS device utilized in the above examples was designed and fabricated (as shown in FIG. 10) to perform the molecular partitioning step of a Microfluidic Systematic Evolution of Ligands by EXponential enrichment (M-SELEX) process.

Materials and Methods a) 4-inch glass wafers (Pyrex 7740 borosilicate glass, Corning, N.Y.) were used for the top and bottom substrates. 20-nm titanium and 200-nm nickel films were patterned on the glass substrate through photolithography and a standard "liftoff" process.

b) Microfluidic vias to the chip were mechanically drilled into the glass substrates using a computer-controlled milling machine (Flashcut CNC, Menlo Park, Calif.). Subsequently, the glass substrates containing the Ni strips were cleaned in acetone, after which a nm $SiO_2$ layer was deposited on the surface via plasma-enhanced chemical vapor deposition (PECVD, Unaxis VLR, Switzerland).

c) A negative-tone master mold of the microfluidic channel was fabricated from PDMS on a 4 inch silicon wafer using a deep reactive-ion-etcher (SLR-770, Plasmatherm, St. Petersburg, Fla.). The PDMS layer was molded and cured at 65° C. for 3 hr.

d) The PDMS layer containing the microfluidic channels was peeled off from the silicon wafer, cleaned with acetone and activated in a UV-ozone chamber for 10 min. Then the PDMS layer was applied to a clean glass substrate.

e) The two substrates were aligned and bonded in a flip-chip aligner (Research Devices M8A, Piscataway, N.J.). Microfluidic inlets and outlets were manually attached to the device with epoxy.

Results

The resulting CMACS device utilizes multi-stream laminar fluidic architecture to achieve extremely high molecular partition efficiencies and uses microfabricated nickel ferromagnetic structures to reproducibly generate magnetophoretic forces to manipulate a small number of magnetic beads. The device has two inlets (Sample and Buffer), which are driven by two independently-controlled syringe pumps, and two outlets (Product and Waste) (FIG. 9, *a*). When a magnetic bead travels through the CMACS device, a combination of hydrodynamic ($F_d$) and magnetophoretic forces ($F_m$) is imposed on them (FIG. 9, b). Assuming spherical geometry of the bead, $F_d$ can be approximated by Stokes' law as $F_d=6\pi\eta \cdot R_p \cdot \upsilon$ (where $\eta$ is the viscosity of the medium, $R_p$ is the bead radius and $\upsilon$ is the velocity). On the other hand, due to the fact that the beads are superparamagnetic, $F_m$ can be approximated as $F_m=m_{sat}\nabla B$ (where $m_{sat}$ is the saturated magnetization of the bead, and B is the magnetic flux density). When an external magnetic field is applied to the CMACS device, the differences in magnetic permeability between the nickel structures ($\mu_{Nickel}$=600%) and the buffer ($\mu_{buffer}$=-$\mu_0$) automatically creates a large magnetic field gradient at their interface, generating $F_m$ that attracts the magnetic beads to the edges of the nickel structures (FIG. 9, c (I)). The CMACS device is designed to operate such that $F_m$ exceeds the component of $F_d$ perpendicular to the nickel strips (i.e., $F_m > F_d \cdot \sin\theta$). Therefore, magnetic beads bound to the desired aptamers are selectively transported from the sample stream into the buffer stream by traveling along the nickel structures (FIG. 9, c (I)). After the magnetic beads reach the buffer stream at the center of the device (FIG. 9, c (II)), they are eluted through the Product outlet. In contrast, unbound oligonucleotides follow the sample stream and are eluted through the Waste outlet (FIG. 9, c (III)). Since the nickel structures are passivated with a thin silicon dioxide layer, there is no direct contact between the nickel structures and the fluids.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A method of screening a library, the method comprising:
contacting a library of candidate agents with a target in a reaction mixture under a condition of high stringency, wherein the condition of high stringency includes providing in the reaction mixture a total number of target molecules that is at least three orders of magnitude less than the total number of library members, wherein said library of candidate agents comprises at least 1,000 chemically distinct species, and wherein said target comprises a magnetic tag that responds to a controllable magnetic field applied to said magnetic tag; and
passing the members of the library through a microfluidic device in a manner that exposes said members to said controllable magnetic field, wherein members of the library of candidate agents that are bound to the target are displaced relative to their unbound counterparts, and wherein the application of the controllable magnetic field provides for a partition efficiency which is greater than $10^6$.

2. The method of claim 1, further comprising isolating unbound candidate agents as agents of interest.

3. The method of claim 1, further comprising isolating members of the library that are bound to the target as agents of interest.

4. The method of claim 1, wherein the condition of high stringency includes a high-stringency salt concentration in the reaction mixture.

5. The method of claim 1, wherein the condition of high stringency includes subjecting the reaction mixture to a high-stringency temperature.

6. The method of claim 1, wherein said method further comprises detecting, amplifying, and/or separating the members of the library that are displaced relative to their unbound counterparts.

7. The method of claim 1, wherein said magnetic tag is a magnetic bead.

8. The method of claim 1, wherein said library is an aptamer library.

9. The method of claim 1, wherein said target is a protein target.

10. The method of claim 1, wherein said target is provided in said reaction mixture at a sub-nanomolar concentration.

11. The method of claim 1, wherein, after one round, the members of the library that are displaced relative to their unbound counterparts bind the target molecule with dissociation constants ($K_d$) in a nanomolar or sub-nanomolar range.

12. A method of screening for candidate agents, the method comprising:
passing a reaction mixture comprising a library of candidate agents and a target through a microfluidic device, wherein said library of candidate agents comprises at least 1,000 chemically distinct species, and wherein said target comprises a magnetic tag that responds to a controllable magnetic field applied to said magnetic tag and wherein said passing exposes said magnetic tag to said controllable magnetic field, and further wherein said target is immobilized by the exposure of said magnetic tag to said controllable magnetic field;
exposing the immobilized target to a condition of high stringency, wherein the condition of high stringency includes providing in the reaction mixture a total number of target molecules that is at least three orders of magnitude less than the total number of library members, wherein said condition of high stringency favors formation of specific target-binding partner complexes, and wherein the method provides a partition efficiency which is greater than $10^6$.

13. The method of claim 12, further comprising identifying unbound candidate agents as agents of interest.

14. The method of claim 12, further comprising identifying target-bound candidate agents as agents of interest.

15. The method of claim 1, wherein the library is a random library.

16. The method of claim 12, wherein the library is a random library.

17. The method of claim 1, wherein the candidate agents are candidate target binding agents (CTBA) and the partition efficiency is defined by the formula:

$$k_{CTBA \cdot T}/k_{CTBA}$$

wherein CTBA·T is the binding complex formed between the target and a CTBA, and wherein $k_{CTBA \cdot T}$ and $k_{CTBA}$ are collection efficiency for CTBA·T and free CTBA, respectively, and are calculated by the formulae:

$$k_{CTBA \cdot T} = CTBA \cdot T_{out}/CTBA \cdot T_{in}$$

$$k_{CTBA} = CTBA_{out}/CTBA_{in}.$$

18. The method of claim 1, wherein the candidate agents are DNA molecules, the target is a protein target, and the partition efficiency is defined by the formula:

$$k_{DNA \cdot T}/k_{DNA}$$

wherein DNA·T is the binding complex formed between the protein target and DNA, and wherein $k_{DNA \cdot T}$ and $k_{DNA}$ are collection efficiency for DNA·T and free DNA, respectively, and are calculated by the formulae:

$$k_{DNA \cdot T} = DNA \cdot T_{out}/DNA \cdot T_{in}$$

$$k_{DNA} = DNA_{out}/DNA_{in}.$$

19. The method of claim 1, wherein said library of candidate agents comprises at least $1 \times 10^{14}$ chemically distinct species.

20. The method of claim 12, wherein the candidate agents are candidate target binding agents (CTBA) and the partition efficiency is defined by the formula:

$$k_{CTBA \cdot T}/k_{CTBA}$$

wherein CTBA·T is the binding complex formed between the target and a CTBA, and wherein $k_{CTBA \cdot T}$ and $k_{CTBA}$ are collection efficiency for CTBA·T and free CTBA, respectively, and are calculated by the formulae:

$$k_{CTBA \cdot T} = CTBA \cdot T_{out}/CTBA \cdot T_{in}$$

$$k_{CTBA} = CTBA_{out}/CTBA_{in}.$$

21. The method of claim 12, wherein the candidate agents are DNA molecules, the target is a protein target, and the partition efficiency is defined by the formula:

$$k_{DNA \cdot T}/k_{DNA}$$

wherein DNA·T is the binding complex formed between the protein target and DNA, and wherein $k_{DNA \cdot T}$ and $k_{DNA}$ are collection efficiency for DNA·T and free DNA, respectively, and are calculated by the formulae:

$$k_{DNA \cdot T} = DNA \cdot T_{out}/DNA \cdot T_{in}$$

$$k_{DNA} = DNA_{out}/DNA_{in}.$$

22. The method of claim 12, wherein said library of candidate agents comprises at least $1 \times 10^{14}$ chemically distinct species.

* * * * *

```
                        SEQUENCE LISTING

<160> NUMBER OF SEQ ID NOS: 7

<210> SEQ ID NO 1
<211> LENGTH: 20
<212> TYPE: DNA
<213> ORGANISM: Artificial Sequence
<220> FEATURE:
<223> OTHER INFORMATION: PCR primer site

<400> SEQUENCE: 1
agcagcacag aggtcagatg                                            20

<210> SEQ ID NO 2
<211> LENGTH: 20
<212> TYPE: DNA
<213> ORGANISM: Artificial Sequence
<220> FEATURE:
<223> OTHER INFORMATION: PCR primer site

<400> SEQUENCE: 2
cctatgcgtg ctaccgtgaa                                            20

<210> SEQ ID NO 3
<211> LENGTH: 98
<212> TYPE: DNA
<213> ORGANISM: Artificial Sequence
<220> FEATURE:
<223> OTHER INFORMATION: DNA template with PCR primer sites

<400> SEQUENCE: 3
agcagcacag aggtcagatg ctttggagac agtccgtggt agggcaggtt ggggtgactt    60
cggaagaagc gagacggtcc tatgcgtgct accgtgaa                            98

<210> SEQ ID NO 4
<211> LENGTH: 60
<212> TYPE: DNA
<213> ORGANISM: Artificial Sequence
<220> FEATURE:
<223> OTHER INFORMATION: Core sequence of selected aptamer

<400> SEQUENCE: 4
tctttcatac cgaggttgat ccagtagtat tcttatctaa tttgttttgt tcgtatgtgc    60

<210> SEQ ID NO 5
<211> LENGTH: 60
<212> TYPE: DNA
```

```
<213> ORGANISM: Artificial Sequence
<220> FEATURE:
<223> OTHER INFORMATION: Core sequence of selected aptamer

<400> SEQUENCE: 5
tggtcttgtc tttcattcca ggtggcgagt caaatcgata ctgatccgct gacacaggat    60

<210> SEQ ID NO 6
<211> LENGTH: 60
<212> TYPE: DNA
<213> ORGANISM: Artificial Sequence
<220> FEATURE:
<223> OTHER INFORMATION: Core sequence of selected aptamer

<400> SEQUENCE: 6
cttgagtgtc atggacgttc cggtcttggg cgggatattt gtttgttttc tgcctatgtt    60

<210> SEQ ID NO 7
<211> LENGTH: 59
<212> TYPE: DNA
<213> ORGANISM: Artificial Sequence
<220> FEATURE:
<223> OTHER INFORMATION: Core sequence of selected aptamer

<400> SEQUENCE: 7
tcagatggcc ggactcaggc actagaccac tatgcttccg ttgccattca tcggcacgt    59
```